US009544700B2

(12) United States Patent
Puria et al.

(10) Patent No.: US 9,544,700 B2
(45) Date of Patent: Jan. 10, 2017

(54) OPTICALLY COUPLED ACTIVE OSSICULAR REPLACEMENT PROSTHESIS

(75) Inventors: Sunil Puria, Sunnyvale, CA (US); Rodney C. Perkins, Woodside, CA (US)

(73) Assignee: EARLENS CORPORATION, Menlo Park, CA (US)

( * ) Notice: Subject to any disclaimer, the term of this patent is extended or adjusted under 35 U.S.C. 154(b) by 329 days.

(21) Appl. No.: 12/814,998

(22) Filed: Jun. 14, 2010

(65) Prior Publication Data

US 2010/0317914 A1    Dec. 16, 2010

Related U.S. Application Data

(60) Provisional application No. 61/187,166, filed on Jun. 15, 2009.

(51) Int. Cl.
*H04R 25/00* (2006.01)
*A61F 2/18* (2006.01)

(52) U.S. Cl.
CPC ....... *H04R 25/606* (2013.01); *A61F 2002/183* (2013.01)

(58) Field of Classification Search
CPC ... H04R 25/606; H04R 2225/67; H04R 25/00; A61N 1/36032
USPC ........... 600/25; 181/126, 128–130; 381/23.1, 381/312–331; 623/10, 24; 607/55–57
See application file for complete search history.

(56) References Cited

U.S. PATENT DOCUMENTS

| 3,209,082 | A | 9/1965 | McCarrell et al. |
| 3,440,314 | A | 4/1969 | Frisch |
| 3,449,768 | A | 6/1969 | Doyle |
| 3,549,818 | A | 12/1970 | Turner et al. |
| 3,585,416 | A | 6/1971 | Mellen |
| 3,594,514 | A | 7/1971 | Wingrove |

(Continued)

FOREIGN PATENT DOCUMENTS

| CN | 1176731 A | 3/1998 |
| CN | 101459868 A | 6/2009 |

(Continued)

OTHER PUBLICATIONS

Atasoy [Paper] "Opto-acoustic Imaging" for BYM504E Biomedical Imaging Systems class at ITU, downloaded from the Internet <<http://www2.itu.edu.tr/~cilesiz/courses/BYM504-2005-OA_504041413.pdf>>, 14 pages, presented May 13, 2005.

(Continued)

*Primary Examiner* — Christine H Matthews
*Assistant Examiner* — Joshua D Lannu
(74) *Attorney, Agent, or Firm* — Wilson, Sonsini, Goodrich & Rosati

(57) ABSTRACT

An active ossicular replacement device is configured to couple the malleus to the stapes, and conduct sound through the vibratory structures of the ear in response to the transmitted electromagnetic energy. The electromagnetic energy may comprise light so as to decrease interference from sources of noise external to the user. The prosthetic device may comprise an assembly that can be implanted in the middle ear in a manner that simplifies surgery. The assembly may comprise a narrow cross-sectional profile such that the assembly can be positioned in the middle ear through an incision in the eardrum, for example without cutting bone that defines the shape of the ear canal or the shape of the middle ear. The prosthetic device can be sized to the user based on a measurement of the ear.

44 Claims, 12 Drawing Sheets

(56) References Cited

U.S. PATENT DOCUMENTS

| | | | |
|---|---|---|---|
| 3,710,399 A | 1/1973 | Hurst | |
| 3,712,962 A | 1/1973 | Epley | |
| 3,764,748 A | 10/1973 | Branch et al. | |
| 3,808,179 A | 4/1974 | Gaylord | |
| 3,870,832 A | 3/1975 | Fredrickson | |
| 3,882,285 A | 5/1975 | Nunley et al. | |
| 3,985,977 A | 10/1976 | Beaty et al. | |
| 4,002,897 A | 1/1977 | Kleinman et al. | |
| 4,061,972 A | 12/1977 | Burgess | |
| 4,075,042 A | 2/1978 | Das | |
| 4,098,277 A | 7/1978 | Mendell | |
| 4,109,116 A | 8/1978 | Victoreen | |
| 4,120,570 A | 10/1978 | Gaylord | |
| 4,207,441 A | 6/1980 | Chouard et al. | |
| 4,248,899 A | 2/1981 | Lyon et al. | |
| 4,252,440 A | 2/1981 | Frosch et al. | |
| 4,281,419 A * | 8/1981 | Treace | 623/10 |
| 4,303,772 A | 12/1981 | Novicky | |
| 4,319,359 A | 3/1982 | Wolf | |
| 4,334,315 A | 6/1982 | Ono et al. | |
| 4,334,321 A | 6/1982 | Edelman | |
| 4,339,954 A | 7/1982 | Anson et al. | |
| 4,357,497 A | 11/1982 | Hochmair et al. | |
| 4,380,689 A | 4/1983 | Giannetti | |
| 4,428,377 A | 1/1984 | Zollner et al. | |
| 4,524,294 A | 6/1985 | Brody | |
| 4,540,761 A | 9/1985 | Kawamura et al. | |
| 4,556,122 A | 12/1985 | Goode | |
| 4,592,087 A | 5/1986 | Killion | |
| 4,606,329 A | 8/1986 | Hough | |
| 4,611,598 A | 9/1986 | Hortmann et al. | |
| 4,628,907 A | 12/1986 | Epley | |
| 4,641,377 A | 2/1987 | Rush et al. | |
| 4,654,554 A | 3/1987 | Kishi | |
| 4,689,819 A | 8/1987 | Killion | |
| 4,696,287 A | 9/1987 | Hortmann et al. | |
| 4,729,366 A | 3/1988 | Schaefer | |
| 4,741,339 A | 5/1988 | Harrison et al. | |
| 4,742,499 A | 5/1988 | Butler | |
| 4,756,312 A | 7/1988 | Epley | |
| 4,766,607 A | 8/1988 | Feldman | |
| 4,774,933 A | 10/1988 | Hough et al. | |
| 4,776,322 A | 10/1988 | Hough et al. | |
| 4,782,818 A | 11/1988 | Mori | |
| 4,800,884 A | 1/1989 | Heide et al. | |
| 4,800,982 A | 1/1989 | Carlson | |
| 4,817,607 A | 4/1989 | Tatge | |
| 4,840,178 A | 6/1989 | Heide et al. | |
| 4,845,755 A | 7/1989 | Busch et al. | |
| 4,865,035 A | 9/1989 | Mori | |
| 4,918,745 A | 4/1990 | Hutchison | |
| 4,932,405 A | 6/1990 | Peeters et al. | |
| 4,936,305 A * | 6/1990 | Ashtiani et al. | 607/57 |
| 4,944,301 A | 7/1990 | Widin et al. | |
| 4,948,855 A | 8/1990 | Novicky | |
| 4,957,478 A | 9/1990 | Maniglia | |
| 4,982,434 A | 1/1991 | Lenhardt et al. | |
| 4,999,819 A | 3/1991 | Newnham et al. | |
| 5,003,608 A | 3/1991 | Carlson | |
| 5,012,520 A | 4/1991 | Steeger | |
| 5,015,224 A | 5/1991 | Mariglia | |
| 5,015,225 A | 5/1991 | Hough et al. | |
| 5,031,219 A | 7/1991 | Ward et al. | |
| 5,061,282 A | 10/1991 | Jacobs | |
| 5,066,091 A | 11/1991 | Stoy et al. | |
| 5,094,108 A | 3/1992 | Kim et al. | |
| 5,117,461 A | 5/1992 | Moseley | |
| 5,142,186 A | 8/1992 | Cross et al. | |
| 5,163,957 A | 11/1992 | Sade et al. | |
| 5,167,235 A | 12/1992 | Seacord et al. | |
| 5,201,007 A | 4/1993 | Ward et al. | |
| 5,259,032 A | 11/1993 | Perkins et al. | |
| 5,272,757 A | 12/1993 | Scofield et al. | |
| 5,276,910 A | 1/1994 | Buchele | |
| 5,277,694 A | 1/1994 | Leysieffer et al. | |
| 5,338,287 A | 8/1994 | Miller et al. | |
| 5,360,388 A | 11/1994 | Spindel et al. | |
| 5,378,933 A | 1/1995 | Pfannenmueller et al. | |
| 5,402,496 A | 3/1995 | Soli et al. | |
| 5,411,467 A | 5/1995 | Hortmann et al. | |
| 5,425,104 A | 6/1995 | Shennib | |
| 5,440,082 A | 8/1995 | Claes | |
| 5,440,237 A | 8/1995 | Brown et al. | |
| 5,455,994 A | 10/1995 | Termeer et al. | |
| 5,456,654 A | 10/1995 | Ball | |
| 5,531,787 A | 7/1996 | Lesinski et al. | |
| 5,531,954 A | 7/1996 | Heide et al. | |
| 5,535,282 A | 7/1996 | Luca | |
| 5,554,096 A | 9/1996 | Ball | |
| 5,558,618 A | 9/1996 | Maniglia | |
| 5,571,148 A | 11/1996 | Loeb et al. | |
| 5,572,594 A | 11/1996 | Devoe et al. | |
| 5,606,621 A | 2/1997 | Reiter et al. | |
| 5,624,376 A | 4/1997 | Ball et al. | |
| 5,707,338 A | 1/1998 | Adams et al. | |
| 5,715,321 A | 2/1998 | Andrea et al. | |
| 5,721,783 A | 2/1998 | Anderson | |
| 5,722,411 A | 3/1998 | Suzuki et al. | |
| 5,729,077 A | 3/1998 | Newnham et al. | |
| 5,740,258 A | 4/1998 | Goodwin-Johansson | |
| 5,749,912 A | 5/1998 | Zhang et al. | |
| 5,762,583 A | 6/1998 | Adams et al. | |
| 5,772,575 A | 6/1998 | Lesinski et al. | |
| 5,774,259 A | 6/1998 | Saitoh et al. | |
| 5,782,744 A | 7/1998 | Money | |
| 5,788,711 A | 8/1998 | Lehner et al. | |
| 5,795,287 A | 8/1998 | Ball et al. | |
| 5,797,834 A | 8/1998 | Goode | |
| 5,800,336 A | 9/1998 | Ball et al. | |
| 5,804,109 A | 9/1998 | Perkins | |
| 5,804,907 A | 9/1998 | Park et al. | |
| 5,814,095 A | 9/1998 | Muller et al. | |
| 5,824,022 A | 10/1998 | Zilberman et al. | |
| 5,825,122 A | 10/1998 | Givargizov et al. | |
| 5,836,863 A | 11/1998 | Bushek et al. | |
| 5,842,967 A | 12/1998 | Kroll | |
| 5,851,199 A | 12/1998 | Peerless et al. | |
| 5,857,958 A | 1/1999 | Ball et al. | |
| 5,859,916 A | 1/1999 | Ball et al. | |
| 5,879,283 A | 3/1999 | Adams et al. | |
| 5,888,187 A | 3/1999 | Jaeger et al. | |
| 5,897,486 A | 4/1999 | Ball et al. | |
| 5,899,847 A | 5/1999 | Adams et al. | |
| 5,900,274 A | 5/1999 | Chatterjee et al. | |
| 5,906,635 A | 5/1999 | Maniglia | |
| 5,913,815 A * | 6/1999 | Ball et al. | 600/25 |
| 5,922,077 A | 7/1999 | Espy et al. | |
| 5,935,170 A | 8/1999 | Haakansson et al. | |
| 5,940,519 A | 8/1999 | Kuo | |
| 5,949,895 A | 9/1999 | Ball et al. | |
| 5,984,859 A | 11/1999 | Lesinski | |
| 5,987,146 A | 11/1999 | Pluvinage et al. | |
| 6,001,129 A * | 12/1999 | Bushek et al. | 623/10 |
| 6,005,955 A | 12/1999 | Kroll et al. | |
| 6,024,717 A | 2/2000 | Ball et al. | |
| 6,038,480 A | 3/2000 | Hrdlicka et al. | |
| 6,045,528 A | 4/2000 | Arenberg et al. | |
| 6,050,933 A | 4/2000 | Bushek et al. | |
| 6,068,589 A | 5/2000 | Neukermans | |
| 6,068,590 A | 5/2000 | Brisken | |
| 6,084,975 A | 7/2000 | Perkins et al. | |
| 6,093,144 A | 7/2000 | Jaeger et al. | |
| 6,137,889 A | 10/2000 | Shennib et al. | |
| 6,139,488 A | 10/2000 | Ball | |
| 6,153,966 A | 11/2000 | Neukermans | |
| 6,174,278 B1 | 1/2001 | Jaeger et al. | |
| 6,181,801 B1 | 1/2001 | Puthuff et al. | |
| 6,190,305 B1 | 2/2001 | Ball et al. | |
| 6,190,306 B1 | 2/2001 | Kennedy | |
| 6,208,445 B1 | 3/2001 | Reime | |
| 6,216,040 B1 | 4/2001 | Harrison | |
| 6,217,508 B1 | 4/2001 | Ball et al. | |
| 6,222,302 B1 | 4/2001 | Imada et al. | |
| 6,222,927 B1 | 4/2001 | Feng et al. | |

(56) References Cited

U.S. PATENT DOCUMENTS

| | | |
|---|---|---|
| 6,240,192 B1 | 5/2001 | Brennan et al. |
| 6,241,767 B1 | 6/2001 | Stennert et al. |
| 6,261,224 B1 | 7/2001 | Adams et al. |
| 6,277,148 B1 | 8/2001 | Dormer |
| 6,312,959 B1 | 11/2001 | Datskos |
| 6,339,648 B1 | 1/2002 | McIntosh et al. |
| 6,342,035 B1 | 1/2002 | Kroll et al. |
| 6,354,990 B1 | 3/2002 | Juneau et al. |
| 6,366,863 B1 | 4/2002 | Bye et al. |
| 6,374,143 B1 | 4/2002 | Berrang et al. |
| 6,385,363 B1 | 5/2002 | Rajic et al. |
| 6,387,039 B1 | 5/2002 | Moses |
| 6,390,971 B1 | 5/2002 | Adams et al. |
| 6,393,130 B1 | 5/2002 | Stonikas et al. |
| 6,422,991 B1 | 7/2002 | Jaeger |
| 6,432,248 B1 | 8/2002 | Popp et al. |
| 6,436,028 B1 | 8/2002 | Dormer |
| 6,438,244 B1 | 8/2002 | Juneau et al. |
| 6,445,799 B1 | 9/2002 | Taenzer et al. |
| 6,473,512 B1 | 10/2002 | Juneau et al. |
| 6,475,134 B1 | 11/2002 | Ball et al. |
| 6,491,622 B1 * | 12/2002 | Kasic et al. .............. 600/25 |
| 6,491,644 B1 | 12/2002 | Vujanic et al. |
| 6,491,722 B1 | 12/2002 | Kroll et al. |
| 6,493,453 B1 | 12/2002 | Glendon |
| 6,493,454 B1 | 12/2002 | Loi et al. |
| 6,498,858 B2 | 12/2002 | Kates |
| 6,507,758 B1 | 1/2003 | Greenberg et al. |
| 6,519,376 B2 | 2/2003 | Biagi et al. |
| 6,536,530 B2 | 3/2003 | Schultz et al. |
| 6,537,200 B2 | 3/2003 | Leysieffer et al. |
| 6,547,715 B1 * | 4/2003 | Muller et al. .............. 600/25 |
| 6,549,633 B1 | 4/2003 | Westermann |
| 6,554,761 B1 | 4/2003 | Puria et al. |
| 6,575,894 B2 | 6/2003 | Leysieffer et al. |
| 6,592,513 B1 | 7/2003 | Kroll et al. |
| 6,603,860 B1 | 8/2003 | Taenzer et al. |
| 6,620,110 B2 | 9/2003 | Schmid |
| 6,626,822 B1 | 9/2003 | Jaeger et al. |
| 6,629,922 B1 | 10/2003 | Puria et al. |
| 6,643,378 B2 | 11/2003 | Schumaier |
| 6,668,062 B1 | 12/2003 | Luo et al. |
| 6,676,592 B2 | 1/2004 | Ball et al. |
| 6,695,943 B2 | 2/2004 | Juneau et al. |
| 6,724,902 B1 | 4/2004 | Shennib et al. |
| 6,728,024 B2 | 4/2004 | Ribak |
| 6,735,318 B2 | 5/2004 | Cho |
| 6,754,358 B1 | 6/2004 | Boesen et al. |
| 6,754,537 B1 | 6/2004 | Harrison et al. |
| 6,801,629 B2 | 10/2004 | Brimhall et al. |
| 6,829,363 B2 | 12/2004 | Sacha |
| 6,842,647 B1 | 1/2005 | Griffith et al. |
| 6,888,949 B1 | 5/2005 | Vanden Berghe et al. |
| 6,900,926 B2 | 5/2005 | Ribak |
| 6,912,289 B2 | 6/2005 | Vonlanthen et al. |
| 6,920,340 B2 | 7/2005 | Laderman |
| 6,931,231 B1 | 8/2005 | Griffin |
| 6,940,989 B1 | 9/2005 | Shennib et al. |
| D512,979 S | 12/2005 | Corcoran et al. |
| 6,975,402 B2 | 12/2005 | Bisson et al. |
| 6,978,159 B2 | 12/2005 | Feng et al. |
| 7,024,010 B2 | 4/2006 | Saunders et al. |
| 7,043,037 B2 | 5/2006 | Lichtblau |
| 7,050,675 B2 | 5/2006 | Zhou |
| 7,057,256 B2 | 6/2006 | Carey, III et al. |
| 7,058,182 B2 | 6/2006 | Kates |
| 7,072,475 B1 | 7/2006 | DeNap et al. |
| 7,076,076 B2 | 7/2006 | Bauman |
| 7,095,981 B1 | 8/2006 | Voroba et al. |
| 7,167,572 B1 | 1/2007 | Harrison et al. |
| 7,174,026 B2 | 2/2007 | Niederdrank |
| 7,179,238 B2 | 2/2007 | Hissong |
| 7,203,331 B2 | 4/2007 | Boesen |
| 7,239,069 B2 | 7/2007 | Cho |
| 7,245,732 B2 | 7/2007 | Jorgensen et al. |
| 7,255,457 B2 | 8/2007 | Ducharme et al. |
| 7,289,639 B2 | 10/2007 | Abel et al. |
| 7,322,930 B2 | 1/2008 | Jaeger et al. |
| 7,349,741 B2 | 3/2008 | Maltan et al. |
| 7,354,792 B2 | 4/2008 | Carey, III et al. |
| 7,376,563 B2 | 5/2008 | Leysieffer et al. |
| 7,390,689 B2 | 6/2008 | Mazur et al. |
| 7,394,909 B1 | 7/2008 | Widmer et al. |
| 7,421,087 B2 | 9/2008 | Perkins et al. |
| 7,424,122 B2 | 9/2008 | Ryan |
| 7,444,877 B2 | 11/2008 | Li et al. |
| 7,547,275 B2 | 6/2009 | Cho |
| 7,630,646 B2 | 12/2009 | Anderson et al. |
| 7,645,877 B2 | 1/2010 | Gmeiner et al. |
| 7,668,325 B2 | 2/2010 | Puria et al. |
| 7,867,160 B2 | 1/2011 | Pluvinage et al. |
| 7,883,535 B2 | 2/2011 | Cantin et al. |
| 7,983,435 B2 | 7/2011 | Moses |
| 8,401,214 B2 | 3/2013 | Perkins et al. |
| 8,545,383 B2 | 10/2013 | Wenzel et al. |
| 8,600,089 B2 | 12/2013 | Wenzel et al. |
| 8,715,153 B2 | 5/2014 | Puria et al. |
| 8,715,154 B2 | 5/2014 | Perkins et al. |
| 8,787,609 B2 | 7/2014 | Perkins et al. |
| 8,845,705 B2 | 9/2014 | Perkins et al. |
| 8,885,860 B2 | 11/2014 | Djalilian et al. |
| 8,986,187 B2 | 3/2015 | Perkins et al. |
| 9,055,379 B2 | 6/2015 | Puria et al. |
| 9,277,335 B2 | 3/2016 | Perkins et al. |
| 2001/0003788 A1 | 6/2001 | Ball et al. |
| 2001/0027342 A1 | 10/2001 | Dormer |
| 2001/0029313 A1 * | 10/2001 | Kennedy .............. 600/25 |
| 2001/0043708 A1 | 11/2001 | Brimhall |
| 2001/0053871 A1 | 12/2001 | Zilberman et al. |
| 2001/0055405 A1 | 12/2001 | Cho |
| 2002/0012438 A1 | 1/2002 | Leysieffer et al. |
| 2002/0029070 A1 | 3/2002 | Leysieffer et al. |
| 2002/0030871 A1 | 3/2002 | Anderson et al. |
| 2002/0035309 A1 | 3/2002 | Leysieffer |
| 2002/0086715 A1 | 7/2002 | Sahagen |
| 2002/0172350 A1 | 11/2002 | Edwards et al. |
| 2002/0183587 A1 | 12/2002 | Dormer |
| 2003/0064746 A1 | 4/2003 | Rader et al. |
| 2003/0097178 A1 * | 5/2003 | Roberson et al. .............. 623/10 |
| 2003/0125602 A1 | 7/2003 | Sokolich et al. |
| 2003/0142841 A1 | 7/2003 | Wiegand |
| 2003/0208099 A1 | 11/2003 | Ball |
| 2003/0220536 A1 | 11/2003 | Hissong |
| 2004/0158157 A1 * | 8/2004 | Jensen et al. .............. 600/476 |
| 2004/0165742 A1 | 8/2004 | Shennib et al. |
| 2004/0184732 A1 | 9/2004 | Zhou |
| 2004/0208333 A1 | 10/2004 | Cheung et al. |
| 2004/0234089 A1 | 11/2004 | Rembrand et al. |
| 2004/0234092 A1 | 11/2004 | Wada et al. |
| 2004/0240691 A1 | 12/2004 | Grafenberg |
| 2005/0020873 A1 | 1/2005 | Berrang et al. |
| 2005/0036639 A1 | 2/2005 | Bachler et al. |
| 2005/0111683 A1 | 5/2005 | Chabries et al. |
| 2005/0163333 A1 * | 7/2005 | Abel et al. .............. 381/315 |
| 2005/0226446 A1 | 10/2005 | Luo et al. |
| 2005/0267549 A1 | 12/2005 | Della Santina et al. |
| 2006/0023908 A1 | 2/2006 | Perkins et al. |
| 2006/0058573 A1 | 3/2006 | Neisz et al. |
| 2006/0062420 A1 | 3/2006 | Araki |
| 2006/0107744 A1 | 5/2006 | Li et al. |
| 2006/0129210 A1 | 6/2006 | Cantin et al. |
| 2006/0161227 A1 | 7/2006 | Walsh et al. |
| 2006/0161255 A1 | 7/2006 | Zarowski et al. |
| 2006/0177079 A1 | 8/2006 | Baekgaard Jensen et al. |
| 2006/0183965 A1 | 8/2006 | Kasic, II et al. |
| 2006/0189841 A1 | 8/2006 | Pluvinage |
| 2006/0231914 A1 | 10/2006 | Carey, III et al. |
| 2006/0233398 A1 | 10/2006 | Husung |
| 2006/0251278 A1 | 11/2006 | Puria et al. |
| 2006/0278245 A1 | 12/2006 | Gan |
| 2007/0083078 A1 | 4/2007 | Easter et al. |
| 2007/0100197 A1 * | 5/2007 | Perkins et al. .............. 600/25 |
| 2007/0127748 A1 | 6/2007 | Carlile et al. |
| 2007/0135870 A1 | 6/2007 | Shanks et al. |

(56) References Cited

U.S. PATENT DOCUMENTS

| | | |
|---|---|---|
| 2007/0161848 A1 | 7/2007 | Dalton et al. |
| 2007/0191673 A1 | 8/2007 | Ball et al. |
| 2007/0225776 A1 | 9/2007 | Fritsch et al. |
| 2007/0236704 A1 | 10/2007 | Carr |
| 2007/0250119 A1 | 10/2007 | Tyler et al. |
| 2007/0251082 A1 | 11/2007 | Milojevic et al. |
| 2007/0286429 A1 | 12/2007 | Grafenberg et al. |
| 2008/0021518 A1 | 1/2008 | Hochmair et al. |
| 2008/0051623 A1 | 2/2008 | Schneider et al. |
| 2008/0077198 A1 | 3/2008 | Webb et al. |
| 2008/0107292 A1 | 5/2008 | Kornagel |
| 2008/0188707 A1 | 8/2008 | Bernard et al. |
| 2008/0298600 A1 | 12/2008 | Poe et al. |
| 2009/0023976 A1 | 1/2009 | Cho et al. |
| 2009/0043149 A1 | 2/2009 | Abel et al. |
| 2009/0092271 A1 | 4/2009 | Fay et al. |
| 2009/0097681 A1 | 4/2009 | Puria et al. |
| 2009/0131742 A1 | 5/2009 | Cho et al. |
| 2009/0141919 A1 | 6/2009 | Spitaels et al. |
| 2009/0157143 A1 | 6/2009 | Edler et al. |
| 2010/0034409 A1 | 2/2010 | Fay et al. |
| 2010/0048982 A1 | 2/2010 | Puria et al. |
| 2010/0114190 A1 | 5/2010 | Bendett et al. |
| 2010/0145135 A1 | 6/2010 | Ball et al. |
| 2010/0272299 A1 | 10/2010 | Van Schuylenbergh et al. |
| 2010/0312040 A1 | 12/2010 | Puria et al. |
| 2011/0125222 A1 | 5/2011 | Perkins et al. |
| 2011/0142274 A1 | 6/2011 | Perkins et al. |
| 2011/0144719 A1 | 6/2011 | Perkins et al. |
| 2011/0152601 A1 | 6/2011 | Puria et al. |
| 2011/0152602 A1 | 6/2011 | Perkins et al. |
| 2011/0152603 A1 | 6/2011 | Perkins et al. |
| 2011/0152976 A1 | 6/2011 | Perkins et al. |
| 2013/0315428 A1 | 11/2013 | Perkins et al. |
| 2014/0275734 A1 | 9/2014 | Perkins et al. |
| 2014/0288358 A1 | 9/2014 | Puria et al. |
| 2015/0031941 A1 | 1/2015 | Perkins et al. |

FOREIGN PATENT DOCUMENTS

| | | |
|---|---|---|
| DE | 2044870 | 3/1972 |
| DE | 3243850 A1 | 5/1984 |
| DE | 3508830 A1 | 9/1986 |
| EP | 0 242 038 A2 | 10/1987 |
| EP | 0 291 325 A2 | 11/1988 |
| EP | 0 296 092 | 12/1988 |
| EP | 0 352 954 A2 | 1/1990 |
| EP | 1035753 A1 | 9/2000 |
| EP | 1435757 A1 | 7/2004 |
| EP | 1 845 919 A1 | 10/2007 |
| EP | 2272520 A1 | 1/2011 |
| FR | 2455820 A1 | 11/1980 |
| GB | 2085694 A | 4/1982 |
| JP | 60-154800 | 8/1985 |
| JP | S621726 B2 | 1/1987 |
| JP | S63252174 A | 10/1988 |
| JP | S6443252 A | 2/1989 |
| JP | 09-327098 | 12/1997 |
| JP | 2004193908 A | 7/2004 |
| JP | 2005516505 A | 6/2005 |
| JP | 2006060833 A | 3/2006 |
| KR | 100624445 B1 | 9/2006 |
| WO | WO 92/09181 A1 | 5/1992 |
| WO | WO 97/36457 A1 | 10/1997 |
| WO | WO 97/45074 A1 | 12/1997 |
| WO | WO 98/06236 A1 | 2/1998 |
| WO | WO 99/03146 | 1/1999 |
| WO | WO 99/15111 | 4/1999 |
| WO | WO-0022875 A2 | 4/2000 |
| WO | WO-0022875 A3 | 7/2000 |
| WO | WO 01/50815 A1 | 7/2001 |
| WO | WO 01/58206 A2 | 8/2001 |
| WO | WO 02/39874 A2 | 5/2002 |
| WO | WO-03030772 A2 | 4/2003 |
| WO | WO 03/063542 A2 | 7/2003 |
| WO | WO 2004/010733 A1 | 1/2004 |
| WO | WO 2005/015952 | 2/2005 |
| WO | WO 2006/042298 A2 | 4/2006 |
| WO | WO-2006039146 A2 | 4/2006 |
| WO | WO 2006/075169 | 7/2006 |
| WO | WO 2006/075175 | 7/2006 |
| WO | WO-2006071210 A1 | 7/2006 |
| WO | WO-2007023164 A1 | 3/2007 |
| WO | WO 2009/047370 A2 | 4/2009 |
| WO | WO 2009/056167 A1 | 5/2009 |
| WO | WO-2009062142 A1 | 5/2009 |
| WO | WO-2009125903 A1 | 10/2009 |
| WO | WO-2010147935 A1 | 12/2010 |
| WO | WO-2010148345 A2 | 12/2010 |

OTHER PUBLICATIONS

Athanassiou et al., "Laser Controlled Photomechanical Actuation of Photochromic Polymers Microsystems" Rev. Adv. Mater. Sci., 2003; 5:245- 251.

Ayatollahi et al., "Design and Modeling of Micromachined Condenser MEMS Loudspeaker using Permanent Magnet Neodymium—Iron—Boron (Nd—Fe—B)," IEEE International Conference on Semiconductor Electronics, 2006. ICSE '06, Oct. 29, 2006-Dec. 1, 2006; pp. 160-166.

Baer et al., "Effects of Low Pass Filtering on the Intelligibility of Speech in Noise for People With and Without Dead Regions at High Frequencies," J Acoust Soc Am. Sep. 2002;112(3 Pt 1):1133-1144.

Best et al., "Influence of High Frequencies on Speech Locatisation," Abstract 981, Feb. 24, 2003, retrieved from: http://www.aro.org/abstracts.html.

Birch et al., "Microengineered Systems for the Hearing Impaired," IEE Colloquium on Medical Applications of Microengineering, Jan. 31, 1996; pp. 2/1-2/5.

Burkhard et al., "Anthropometric Manikin for Acoustic Research," J Acoust Soc Am. Jul. 1975;58(1):214-22.

Camacho-Lopez et al., "Fast Liquid Crystal Elastomer Swims Into the Dark," Electronic Liquid Crystal Communications, (Nov. 26, 2003), 9 pages total.

Carlile et al., Abstract 1264—"Spatialisation of Talkers and the Segregation of Concurrent Speech ," Feb. 24, 2004, retrieved from: http://www.aro.org/archives/2004/2004_1264.html.

Cheng et al., "A Silicon Microspeaker for Hearing Instruments," Journal of Micromechanics and Microengineering 2004; 14(7):859-866.

Datskos et al., "Photoinduced and Thermal Stress in Silicon Microcantilevers", Applied Physics Letters, Oct. 19, 1998; 73(16):2319-2321.

Decraemer et al., "A Method for Determining Three-Dimensional Vibration in the Ear," Hearing Research, 77 (1-2): 19-37 (1994).

"Ear", Retrieved from the Internet: <<http://wwwmgs.bionet.nsc.ru/mgs/gnw/trrd/thesaurus/Se/ear.html>>, downloaded on Jun. 17, 2008, 4 pages total.

Fay, "Cat Ear Drum Mechanics," Ph.D. thesis, Dissertation submitted to Department of Aeronautics and Astronautics, Stanford University, May 2001, 210 pages total.

Fay et al., "Cat Eardrum Response Mechanics," in Calladine Festschrift, edited by S. Pellegrino Kluwer Academic Publishers, The Netherlands, 2002; 10 pages total.

Fletcher, "Effects of Distortion on the Individual Speech Sounds", Chapter 18, *ASA Edition of Speech and Hearing in Communication*, Acoust Soc.of Am. (republished in 1995) pp. 415-423.

Freyman et al., "Spatial Release from Informational Masking in Speech Recognition," J Acoust Soc Am. May 2001;109(5 Pt 1):2112-2122.

Freyman et al., "The Role of Perceived Spatial Separation in the Unmasking of Speech," J Acoust Soc Am. Dec. 1999;106(6):3578-3588.

Gennum, GA3280 Preliminary Data Sheet: Voyageur TD Open Platform DSP System for Ultra Low Audio Processing, downloaded from the Internet: <<http://www.sounddesigntechnologies.com/products/pdf/37601DOC.pdf>>, Oct. 2006; 17 pages.

(56) References Cited

OTHER PUBLICATIONS

Gobin et al; "Comments on the Physical Basis of the Active Materials Concept" Proc. SPIE 4512:84-92.
Hato et al., "Three-Dimensional Stapes Footplate Motion in Human Temporal Bones." Audiol Neurootol , 2003; 8: 140-152.
"Headphones" Wikipedia Entry, downloaded from the Internet : <<http://en.wikipedia.org/wiki/Headphones>>, downloaded on Oct. 27, 2008, 7 pages total.
Hofman et al., "Relearning Sound Localization With New Ears," Nat Neurosci. Sep. 1998;1(5):417-421.
Izzo et al., "Laser Stimulation of the Auditory Nerve," Lasers Surg Med. Sep. 2006;38(8):745-753.
Izzo et al, "Laser Stimulation of Auditory Neurons: Effect of Shorter Pulse Duration and Penetration Depth," Biophys J. Apr. 15, 2008;94(8):3159-3166.
Izzo et al., "Selectivity of Neural Stimulation in the Auditory System: A Comparison of Optic and Electric Stimuli," J Biomed Opt. Mar.-Apr. 2007;12(2):021008.
Jin et al., "Speech Localization", J. Audio Eng. Soc. convention paper, presented at the *AES* 112th Convention, Munich, Germany, May 10-13, 2002, 13 pages total.
Killion, "Myths About Hearing Noise and Directional Microphones," *The Hearing Review*, vol. 11, No. 2, (Feb. 2004), pp. 14, 16, 18, 19, 72 & 73.
Killion, "SNR loss: I can hear what people say but I can't understand them," The Hearing Review, 1997; 4(12):8-14.
Lee et al., "A Novel Opto-Electromagnetic Actuator Coupled to the tympanic Membrane" Journal of Biomechanics, 2008; 41(16): 3515-3518.
Lee et al., "The Optimal Magnetic Force for a Novel Actuator Coupled to the Tympanic Membrane: A Finite Element Analysis," Biomedical Engineering: Applications, Basis and Communications, 2007; 19(3):171-177.
Lezal, "Chalcogenide Glasses—Survey and Progress", J. Optoelectron Adv Mater., Mar. 2003; 5 (1):23-34.
Markoff, "Intuition + Money: An Aha Moment," New York Times Oct. 11, 2008, p. BU4, 3 pages total.
Martin et al. "Utility of Monaural Spectral Cues is Enhanced in the Presence of Cues to Sound-Source Lateral Angle," JARO, 2004; 5:80-89.
Moore, "Loudness Perception and Intensity Resolution", *Cochlear Hearing Loss*, Whurr Publishers Ltd., (1998), Chapter 4, pp. 90-115.
Murugasu et al., "Malleus-to-footplate versus malleus-to-stapes-head ossicular reconstruction prostheses: temporal bone pressure gain measurements and clinical audiological data," Otol Neurotol. Jul. 2005;26(4):572-582.
Musicant et al., "Direction-Dependent Spectral Properties of Cat External Ear: New Data and Cross-Species Comparisons," J. Acostic. Soc. Am, May 10-13, 2002, Feb. 1990; 8(2):757-781.
National Semiconductor, LM4673 Boomer: Filterless, 2.65W, Mono, Class D Audio Power Amplifier, [Data Sheet] downloaded from the Internet: <<http://www.national.com/ds/LM/LM4673.pdf>>; Nov. 1, 2007; 24 pages.
O'Connor et al., "Middle ear Cavity and Ear Canal Pressure-Driven Stapes Velocity Responses in Human Cadaveric Temporal Bones," J Acoust Soc Am. Sep. 2006;120(3):1517-28.
Perkins et al., "The EarLens System: New sound transduction methods," Hear Res. Feb. 2, 2010; 10 pages total.
Poosanaas et al., "Influence of Sample thickness on the performance of Photostrictive ceramics," J. App. Phys., Aug. 1998; 84(3):1508-1512.
Puria et al., "Abstract 1112: A Gear in the Middle Ear," ARO Thirtieth Annual MWM, Denver CO, Feb. 13, 2007.
Puria et al., "Malleus-to-Footplate Ossicular Reconstruction Prosthesis Positioning: Cochleovestibular Pressure Optimization", Otol Neurotol. May 2005;26(3):368-379.
Puria and Allen, "Measurements and Model of the Cat Middle Ear: Evidence of Tympanic Membrane Acoustic Delay," Journal of the Acoustical Society of America,.1998; 104 (6):3463-3481.
Puria et al., "Middle Ear Morphometry From Cadaveric Temporal Bone MicroCT Imaging," Proceedings of the 4th International Symposium, Zurich, Switzerland, Jul. 27-30, 2006, Middle Ear Mechanics in Research and Otology, pp. 259-268.
Puria et al., "Sound-Pressure Measurements in the Cochlear Vestibule of Human-Cadaver Ears," Journal of the Acoustical Society of America, 101 (5-1): 2754-2770, (1997).
Roush, "SiOnyx Brings "Black Silicon" into the Light; Material Could Upend Solar, Imaging Industries," Xconomy, Oct. 12, 2008, retrieved from the Internet: <<http://www.xconomy.com/boston/2008/10/12/sionyx-brings-black-silicon-into-the-light-material-could-upend-solar-imaging-industries/>> 4 pages total.
Rubinstein, "How Cochlear Implants Encode Speech," Curr Opin Otolaryngol Head Neck Surg. Oct. 2004;12(5):444-8; retrieved from the Internet: <http://www.ohsu.edu/nod/documents/week3/Rubenstein.pdf>.
Sekaric et al., "Nanomechanical Resonant Structures as Tunable Passive Modulators," App. Phys. Lett., Nov. 2003; 80(19): 3617-3619.
Sound Design Technologies, "VoyagerTD™ Open Platform DSP System for Ultra Low Power Audio Processing—GA3280 Data Sheet", Oct. 2007; retrieved from the Internet: <<http://www.sounddes.com/pdf/37601DOC.pdf>>, 15 pages total.
Shaw, "Transformation of Sound Pressure Level From the Free Field to the Eardrum in the Horizontal Plane," J. Acoust. Soc. Am., Dec. 1974; 56(6):1848-1861.
Shih, "Shape and Displacement Control of Beams with Various Boundary Conditions via Photostrictive optical actuators," Proc. IMECE (Nov. 2003), pp. 1-10.
Shock, "How Deep Brain Stimulation Works for Parkinson's Disease" [website]; retrieved from the Internet: <http://www.shockmd.com/2009/05/11/how-deep-brain-stimulation-works-for-parkinsons-disease/> on Jun. 18, 2010, 6 pages total.
Stenfelt et al., "Bone-Conducted Sound: Physiological and Clinical Aspects," Otology & Neurotology, Nov. 2005; 26 (6):1245-1261.
Stuchlik et al, "Micro-Nano Actuators Driven by Polarized Light", IEEE Proc. Sci. Meas. Techn. Mar. 2004, 151(2):131-136.
Suski et al., "Optically Activated ZnO/SiO2/Si Cantilever Beams", Sensors & Actuators, 1990; 24:221-225.
Takagi et al.; "Mechanochemical Synthesis of Piezoelectric PLZT Powder", KONA, 2003, 151(21):234-241.
Thakoor et al., "Optical Microactuation in Piezoceramics", Proc. SPIE, Jul. 1998; 3328:376-391.
Tzou et al; "Smart Materials, Precision Sensors/Actuators, Smart Structures, and Structronic Systems", Mechanics of Advanced Materials and Structures, 2004;11:367-393.
Uchino et al.; "Photostricitve actuators," *Ferroelectrics* 2001; 258:147-158.
Vickers et al., "Effects of Low-Pass Filtering on the Intelligibility of Speech in Quiet for People With and Without Dead Regions at High Frequencies," *J Acoust Soc Am*. Aug. 2001;110(2):1164-1175.
Vinikman-Pinhasi et al., "Piezoelectric and Piezoopctic Effects in Porous Silicon," Applied Physics Letters, Mar. 2006; 88(11): 111905-111906.
Wang et al., "Preliminary Assessment of Remote Photoelectric Excitation of an Actuator for a Hearing Implant," Proceeding of the 2005 IEEE, Engineering in Medicine and Biology 27th Annual Conference, Shanghai, China, Sep. 1-4, 2005, pp. 6233-6234.
Wiener et al., "On the Sound Pressure Transformation by the Head and Auditory Meatus of the Cat", Acta Otolaryngol. Mar. 1966;61(3):255-269.
Wightman et al., "Monaural Sound Localization Revisited," J Acoust Soc Am. Feb. 1997;101(2):1050-1063.
Yi et al., "Piezoelectric Microspeaker with Compressive Nitride Diaphragm," The Fifteenth IEEE International Conference on Micro Electro Mechanical Systems, 2002; pp. 260-263.
Yu et al. "Directed Bending of a Polymer Film by Light", Nature, Sep. 2003; 425(6954):145.
International Search Report and Written Opinion of PCT Application No. PCT/US2010/038602, mailed Aug. 27, 2010, 15 pages total.
U.S. Appl. No. 60/702,532, filed Jul. 25, 2005, inventor: Nikolai Aljuri.

(56) References Cited

OTHER PUBLICATIONS

U.S. Appl. No. 61/099,087, filed Sep. 22, 2008, inventor: Paul Rucker.
Fay, et al. Preliminary evaluation of a light-based contact hearing device for the hearing impaired. Otol Neurotol. Jul. 2013;34(5):912-21. doi: 10.1097/MAO.0b013e31827de4b1.
Dictionary.com's (via American Heritage Medical Dictionary) online dictionary definition of 'percutaneous'. Accessed on Jun. 3, 2013. 2 pages.
Merriam-Webster's online dictionary definition of 'percutaneous'. Accessed on Jun. 3, 2013. 3 pages.
Ear. Retrieved from the Internet: http://wwwmgs.bionet.nsc.ru/mgs/gnw/trrd/thesaurus/Se/ear.html. Accessed Jun. 17, 2008.
European search report and search opinion dated Jun. 5, 2013 for EP Application No. 10797560.9.
European search report and search opinion dated Oct. 24, 2012 for EP Application No. 10797545.0.
European search report and search opinion dated Nov. 5, 2013 for EP Application No. 10790292.
Hakansson, et al. Percutaneous vs. transcutaneous transducers for hearing by direct bone conduction (Abstract). Otolaryngol Head Neck Surg. Apr. 1990;102(4):339-44.
International search report and written opinion dated Jan. 18, 2011 for PCT/US2010/039240.
International search report and written opinion dated Jan. 28, 2011 for PCT/US2010/039347.
International search report and written opinion dated Sep. 28, 2010 for PCT/US2010/039209.
International search report and written opinion dated Oct. 29, 2010 for PCT/US2010/037509.
International search report dated Jan. 28, 2011 for PCT/US2010/039445.
International search report dated Mar. 29, 2011 for PCT/US2010/039776.
MAH. Fundamentals of photovoltaic materials. National Solar Power Research Institute. Dec. 21, 1998, 3-9.
"Notice of allowance dated Jan. 28, 2013 for U.S. Appl. No. 12/818,449."
"Notice of allowance dated Mar. 27, 2015 for U.S. Appl. No. 12/794,969."
Notice of allowance dated Apr. 7, 2014 for U.S. Appl. No. 13/770,106.
Notice of allowance dated Jul. 2, 2014 for U.S. Appl. No. 12/822,810.
Notice of allowance dated Dec. 21, 2012 for U.S. Appl. No. 12/818,449.
"Office action dated Jan. 29, 2013 for U.S. Appl. No. 12/794,969."
Office action dated Feb. 25, 2013 for U.S. Appl. No. 12/822,810.
"Office action dated Feb. 27, 2014 for U.S. Appl. No. 12/820,776."
"Office action dated Mar. 3, 2015 for U.S. Appl. No. 14/219,180."
"Office action dated Mar. 16, 2015 for U.S. Appl. No. 12/820,776."
"Office action dated Apr. 10, 2015 for U.S. Appl. No. 14/300,441."
"Office action dated Apr. 25, 2014 for U.S. Appl. No. 12/794,969."
Office action dated Jul. 2, 2013 for U.S. Appl. No. 12/818,434.
Office action dated Jul. 30, 2014 for U.S. Appl. No. 12/818,434.
Office action dated Aug. 3, 2012 for U.S. Appl. No. 12/822,810.
"Office action dated Aug. 13, 2013 for U.S. Appl. No. 12/820,776."
Office action dated Aug. 15, 2013 for U.S. Appl. No. 12/820,767.
"Office action dated Aug. 22, 2014 for U.S. Appl. No. 12/820,776."
"Office action dated Sep. 8, 2015 for U.S. Appl. No. 12/818,434."
Office action dated Sep. 12, 2013 for U.S. Appl. No. 12/822,810.
Office action dated Sep. 24, 2013 for U.S. Appl. No. 13/770,106.
"Office action dated Oct. 3, 2013 for U.S. Appl. No. 12/794,969."
Office action dated Oct. 23, 2012 for U.S. Appl. No. 12/818,434.
"Office action dated Nov. 3, 2014 for U.S. Appl. No. 12/794,969."
Office action dated Nov. 19, 2013 for U.S. Appl. No. 12/818,434.
"Office action dated Nov. 21, 2012 for U.S. Appl. No. 12/820,776."
Office action dated Nov. 23, 2012 for U.S. Appl. No. 12/820,767.
"Office action dated Dec. 19, 2014 for U.S. Appl. No. 12/818,434."
Robles, et al. Mechanics of the mammalian cochlea. Physiol Rev. Jul. 2001;81(3):1305-52.
Web Books Publishing, "The Ear," accessed online Jan. 22, 2013, available online Nov. 2, 2007 at http://www.web-books.com/eLibrary/Medicine/Physiology/Ear/Ear.htm.
Fritsch, et al. EarLens transducer behavior in high-field strength MRI scanners. Otolaryngol Head Neck Surg. Mar. 2009;140(3):426-8. doi: 10.1016/j.otohns.2008.10.016.
Gantz, et al. Broad Spectrum Amplification with a Light Driven Hearing System. Combined Otolaryngology Spring Meetings, 2016 (Chicago).
Gantz, et al. Light Driven Hearing Aid: A Multi-Center Clinical Study. Association for Research in Otolaryngology Annual Meeting, 2016 (San Diego).
Gantz, et al. Light-Driven Contact Hearing Aid for Broad Spectrum Amplification: Safety and Effectiveness Pivotal Study. Otology & Neurotology Journal, 2016 (in review).
Jian, et al. A 0.6 V, 1.66 mW energy harvester and audio driver for tympanic membrane transducer with wirelessly optical signal and power transfer. InCircuits and Systems (ISCAS), 2014 IEEE International Symposium on Jun. 1, 2014. 874-7. IEEE.
Khaleghi, et al. Characterization of Ear-Canal Feedback Pressure dut to Umbo-Drive Forces: Finite-Element vs. Circuit Models. ARO Midwinter Meeting 2016, (San Diego).
Levy, et al. Characterization of the available feedback gain margin at two device microphone locations, in the fossa triangularis and Behind the Ear, for the light-based contact hearing device. Acoustical Society of America (ASA) meeting, 2013 (San Francisco).
Levy, et al. Extended High-Frequency Bandwidth Improves Speech Reception in the Presence of Spatially Separated Masking Speech. Ear Hear. Sep.-Oct. 2015;36(5):e214-24. doi: 10.1097/AUD.0000000000000161.
Moore, et al. Spectro-temporal characteristics of speech at high frequencies, and the potential for restoration of audibility to people with mild-to-moderate hearing loss. Ear Hear. Dec. 2008;29(6):907-22. doi: 10.1097/AUD.0b013e31818246f6.
Perkins, et al. Light-based Contact Hearing Device: Characterization of available Feedback Gain Margin at two device microphone locations. Presented at AAO-HNSF Annual Meeting, 2013 (Vancouver).
Perkins, et al. The EarLens Photonic Transducer: Extended bandwidth. Presented at AAO-HNSF Annual Meeting, 2011 (San Francisco).
Perkins, R. Earlens tympanic contact transducer: a new method of sound transduction to the human ear. Otolaryngol Head Neck Surg. Jun. 1996;114(6):720-8.
Puria, et al. Cues above 4 kilohertz can improve spatially separated speech recognition. The Journal of the Acoustical Society of America, 2011, 129, 2384.
Puria, et al. Extending bandwidth above 4 kHz improves speech understanding in the presence of masking speech. Association for Research in Otolaryngology Annual Meeting, 2012 (San Diego).
Puria, et al. Extending bandwidth provides the brain what it needs to improve hearing in noise. First international conference on cognitive hearing science for communication, 2011 (Linkoping, Sweden).
Puria, et al. Hearing Restoration: Improved Multi-talker Speech Understanding. 5th International Symposium on Middle Ear Mechanics In Research and Otology (MEMRO), Jun. 2009 (Stanford University).
Puria, et al. Imaging, Physiology and Biomechanics of the middle ear: Towards understating the functional consequences of anatomy. Stanford Mechanics and Computation Symposium, 2005, et Fong J.
Puria, et al. Temporal-Bone Measurements of the Maximum Equivalent Pressure Output and Maximum Stable Gain of a Light-Driven Hearing System That Mechanically Stimulates the Umbo. Otol Neurotol. Feb. 2016;37(2):160-6. doi: 10.1097/MAO.0000000000000941.
Puria, et al. The EarLens Photonic Hearing Aid. Association for Research in Otolaryngology Annual Meeting, 2012 (San Diego).
Puria, et al. The Effects of bandwidth and microphone location on understanding of masked speech by normal-hearing and hearing-

(56) References Cited

OTHER PUBLICATIONS impaired listeners. International Conference for Hearing Aid Research (IHCON) meeting, 2012 (Tahoe City).

Puria. Measurements of human middle ear forward and reverse acoustics: implications for otoacoustic emissions. J Acoust Soc Am. May 2003;113(5):2773-89.

Puria, S. Middle Ear Hearing Devices. Chapter 10. Part of the series Springer Handbook of Auditory Research pp. 273-308. Date: Feb. 9, 2013.

Song, et al. The development of a non-surgical direct drive hearing device with a wireless actuator coupled to the tympanic membrane. Applied Acoustics. Dec. 31, 2013;74(12):1511-8.

\* cited by examiner

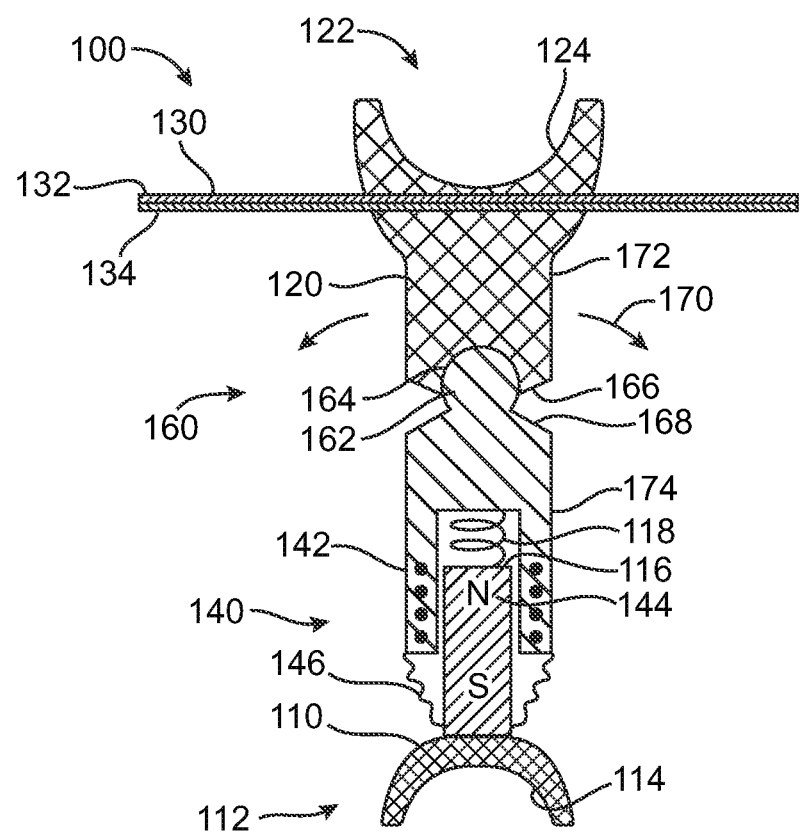
FIG. 1E1

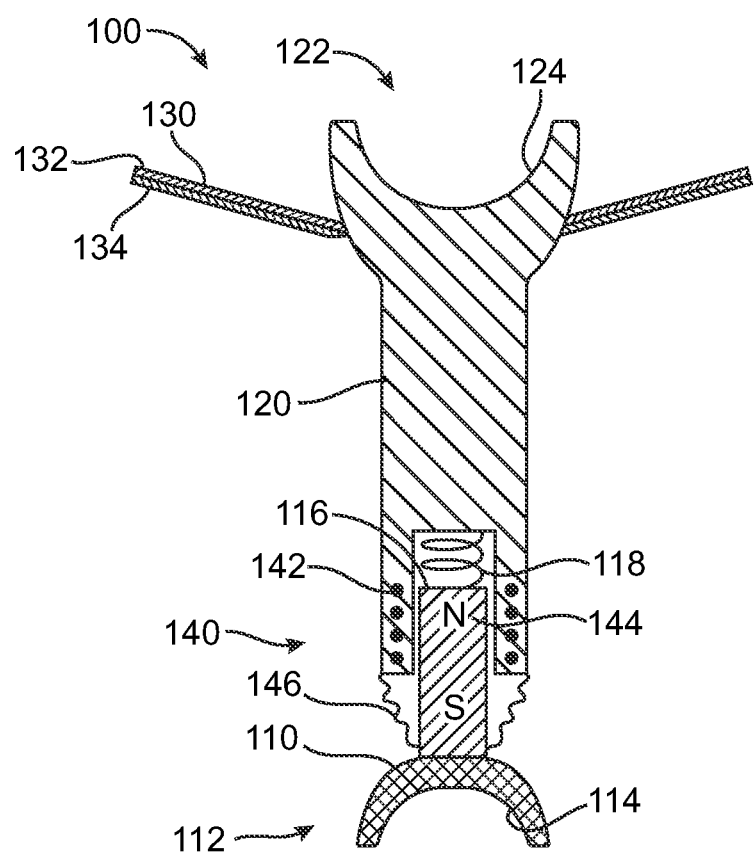
FIG. 1E2

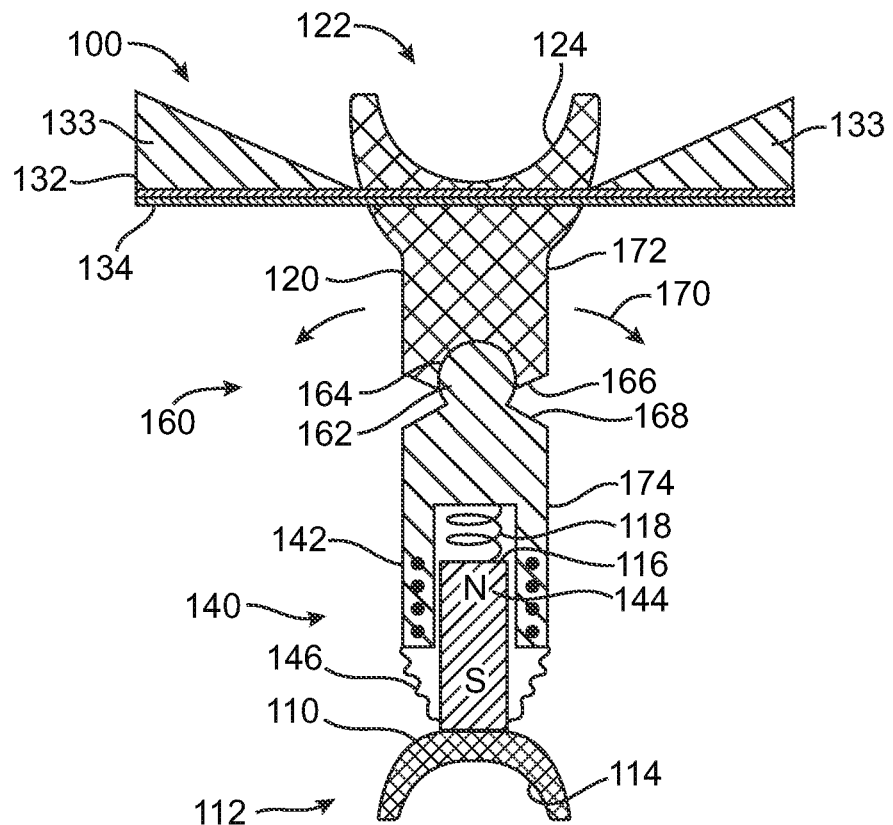
FIG. 1E3
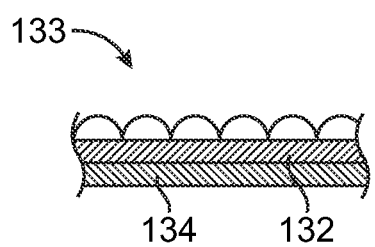
FIG. 1E4

OPTICALLY COUPLED ACTIVE OSSICULAR REPLACEMENT PROSTHESIS

CROSS-REFERENCES TO RELATED APPLICATIONS

The present application claims priority to U.S. App. No. 61/187,166 filed Jun. 15, 2009, entitled "Optically Coupled Active Ossicular Replacement Prosthesis", the full disclosure of which is incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

1. Field of the Invention

The present invention is related to hearing systems, devices and methods. Although specific reference is made to hearing aid systems and prostheses, embodiments of the present invention can be used in many applications in which a signal is used to stimulate the ear.

People like to hear. Hearing allows people to listen to and understand others. Natural hearing can include spatial cues that allow a user to hear a speaker, even when background noise is present. Natural hearing can include orientation cues that allows a listener to determine the spatial location of a sound in at least some instances. People also like to communicate with those who are far away, such as with cellular phones.

Hearing devices can be used with communication systems to help the hearing impaired and to help people communicate with others who are far away. At least some hearing impaired people have a mixed hearing loss. With mixed hearing loss, a person may have a conductive hearing loss that occurs in combination with a sensorineural hearing loss. The conductive hearing loss may be due to diminished function of the conductive components of the ear such as the eardrum and ossicles that transmit sound from the ear canal to the cochlea. The sensorineural hearing loss may comprise diminished function of the cochlea, such that the cochlea does not convert sound waves to neural impulses as effectively as would be ideal.

Many of the prior therapies for mixed hearing loss are less than ideal in at least some instances. One approach has been to replace, at least partially, one or more of the ossicles of the middle ear with an ossicular replacement prosthesis. Although the ossicular replacement prosthesis can improve the conductive portion of the mixed hearing loss, such treatment may leave the patient with diminished hearing due to the remaining sensorineural hearing loss in at least some instances.

At least some of the patients who receive an ossicular replacement prosthesis may use hearing aids following surgery in at least some instances. Although hearing aids can help some, many of the prior hearing aids do not offer the sound localization cues of natural hearing, as placement of a microphone in the ear canal to detect the sound localization cues can result in feedback in at least some instances. Further, at least some of the prior hearing devices can result in occlusion, which can be a tunnel-like hearing effect and may be caused by large hearing aids which block the ear canal in at least some instances. Occlusion may be noticed by the user when he or she speaks and can result in an unnatural sound during speech.

For the above reasons, it would be desirable to provide hearing systems which at least decrease, or even avoid, at least some of the above mentioned limitations of the current prosthetic devices. For example, there is a need to provide a hearing prosthesis which provides hearing with natural qualities, for example with spatial information cues, and which allow the user to hear with less occlusion, distortion and feedback than current devices.

2. Description of the Background Art

Patents and publications that may be relevant to the present application include: U.S. Pat. Nos. 3,585,416; 3,764,748; 3,882,285; 5,142,186; 5,554,096; 5,624,376; 5,795,287; 5,800,336; 5,825,122; 5,857,958; 5,859,916; 5,888,187; 5,897,486; 5,913,815; 5,949,895; 6,005,955; 6,068,590; 6,093,144; 6,139,488; 6,174,278; 6,190,305; 6,208,445; 6,217,508; 6,222,302; 6,241,767; 6,422,991; 6,475,134; 6,519,376; 6,620,110; 6,626,822; 6,676,592; 6,728,024; 6,735,318; 6,900,926; 6,920,340; 7,072,475; 7,095,981; 7,239,069; 7,289,639; D512,979; 2002/0086715; 2003/0142841; 2004/0234092; 2005/0020873; 2006/0107744; 2006/0233398; 2006/075175; 2007/0083078; 2007/0191673; 2008/0021518; 2008/0107292; commonly owned U.S. Pat. Nos. 5,259,032; 5,276,910; 5,425,104; 5,804,109; 6,084,975; 6,554,761; 6,629,922; U.S. Publication Nos. 2006/0023908; 2006/0189841; 2006/0251278; and 2007/0100197. Non-U.S. patents and publications that may be relevant include EP1845919 PCT Publication Nos. WO 03/063542; WO 2006/075175; U.S. Publication Nos. Journal publications that may be relevant include: Ayatollahi et al., "Design and Modeling of Micromachines Condenser MEMS Loudspeaker using Permanent Magnet Neodymium-Iron-Boron (Nd—Fe—B)", ISCE, Kuala Lampur, 2006; Birch et al, "Microengineered Systems for the Hearing Impaired", IEE, London, 1996; Cheng et al., "A silicon microspeaker for hearing instruments", J. Micromech. Microeng., 14 (2004) 859-866; Yi et al., "Piezoelectric microspeaker with compressive nitride diaphragm", IEEE, 2006, and Zhigang Wang et al., "Preliminary Assessment of Remote Photoelectric Excitation of an Actuator for a Hearing Implant", IEEE Engineering in Medicine and Biology 27th Annual Conference, Shanghai, China, Sep. 1-4, 2005. Other publications of interest include: Gennum GA3280 Preliminary Data Sheet, "Voyager TDTM. Open Platform DSP System for Ultra Low Power Audio Processing" and National Semiconductor LM4673 Data Sheet, "LM4673 Filterless, 2.65 W, Mono, Class D audio Power Amplifier"; Puria, S. et al., Middle ear morphometry from cadaveric temporal bone micro CT imaging, Invited Talk. MEMRO 2006, Zurich; Puria, S. et al, A gear in the middle ear ARO 2007, Baltimore, Md.; Puria et al, Malleus-to-Footplate Ossicular Reconstruction Prosthesis Positioning: Cochleovestibular pressure optimization, Otology and Neurology, 26(368-379), 2005; Murugasu et al, Malleus-to-Footplate versus Malleus-to-Stapes-Head Ossicular Reconstruction Prosthesis: Temporal Bone Pressure Gain Measurements and Clinical Audiological Data, Otology and Neurology, 26(572-582), 2005; Lee et al., "The Optimal Magnetic Force For A Novel Actuator Coupled to the Tympanic Membrane: A Finite Element Analysis," Biomedical Engineering: Applications, Basis and Communications, Vol. 19, No. 3(171-177), 2007.

BRIEF SUMMARY OF THE INVENTION

The present invention is related to hearing systems, devices and methods. Although specific reference is made to hearing aid systems, embodiments of the present invention can be used in many applications in which a signal is used to stimulate the ear, for example cellular communication and entertainment systems.

Embodiments of the present invention can provide improved hearing prosthesis which overcomes at least some of the aforementioned limitations of current systems. The prosthesis may comprise an active ossicular replacement prosthesis (hereinafter "AORP"). The active ossicular replacement device can be configured to couple the malleus to the stapes, and conduct sound through the vibratory structures of the ear in response to electromagnetic energy transmitted wirelessly to the AORP. The wirelessly transmitted electromagnetic energy may comprise an oscillating electric and magnetic field such as from a coil, or may comprise light so as to decrease interference from sources of noise external to the user. The AORP may comprise an assembly that can be implanted in the middle ear in a manner that simplifies surgery. The assembly may comprise a narrow cross-sectional profile such that the assembly can be positioned in the middle ear through an incision in the eardrum, for example without cutting bone that defines the shape of the ear canal or the shape of the middle ear. The AORP can be sized to the user so as to fit between the malleus and stapes, for example sized based on a measurement of the ear during surgery. The incision can be closed and electromagnetic energy transmitted through the closed incision to a transducer configured to vibrate the ear in response to the electromagnetic energy. In some embodiments, the AORP comprises a first component coupled to a second component with transducer, such that the transducer can change a distance extending along an axial length from the first end to the second end so as to vibrate the ear and transmit the sound to the user. The lateral component may comprise a mass greater than the medial component such that the stapes vibrates more than the tympanic membrane so as to decrease feedback, such that the user can hear sound localization cues with frequencies above about 4 kHz from a microphone located in the ear canal or near the opening to the ear canal. For example, a microphone can be positioned in the ear canal with reduced feed back as the eardrum can be displaced with the lateral component less than the stapes is displaced with the medial component. Also, the AORP may be coupled to the malleus at a location between the umbo and the head so as to decrease occlusion.

In a first aspect, embodiments, of the present invention provide an active ossicular replacement device. The device comprises a first end configured to connect with at least one of an eardrum or a malleus of the ear. A second end is configured to connect with a stapes of the ear, the first end opposite the second end. At least one transducer is configured to vibrate at least the second end in response to the electromagnetic energy.

In many embodiments, the at least one transducer is configured to receive electromagnetic energy transmitted through tissue of the user. For example, the tissue may comprise tissue of the eardrum of the user.

In many embodiments, the first end, the second end and the at least one transducer comprise an assembly are configured for placement in the middle ear between the malleus and the stapes. A distance from the first end to the second end is within a range from about 2.5 mm to about 7.5 such that the assembly fits between the malleus and the stapes.

In many embodiments, the first end comprises a recess shaped to receive at least a portion of the malleus. The recess may comprise concave surface can be shaped to receive at least a portion of a manubrium of the malleus extending between a head of the malleus and an umbo. The recess may extend inward a maximum distance of no more than about 0.6 mm to receive the portion of the manubrium, and the recess may comprise a width within a range from about 0.7 mm to about 0.9 mm.

In many embodiments, the second end is shaped to couple the stapes. For example, the second end can be shaped to couple to a head of the stapes. The second end may comprise a recess shaped to couple to the head of the stapes. The recess may extend inward a distance within a first range from about 0.6 mm to about 0.9 mm, and the recess may comprise a distance across within a second range from about 1.1 mm to about 1.3 mm. Alternatively, the second end may be shaped to couple a footplate of the stapes. For example, the second end may comprise at least one of a flat surface or a convex surface to couple to the footplate of the stapes.

In many embodiments, the at least one transducer comprises a movement transducer comprising at least one of a piezoelectric transducer, a coil, a magnet, a balanced armature transducer, or a photostrictive material. The at least one transducer may further comprise a second at least one transducer configured to receive the electromagnetic energy transmitted through the eardrum, in which the second at least one transducer comprises at least one of a photodetector or a coil configured to receive the electromagnetic energy transmitted wirelessly through the eardrum. For example, the second at least one transducer may comprise the photodetector and the electromagnetic energy transmitted through the eardrum may comprise light. The photodetector may comprise a first photodetector configured to receive a first at least one wavelength of light and a second photodetector configured to receive a second at least one wavelength of light, and the first photodetector and the second photodetector can be coupled to the movement transducer so as to urge the first end toward the second end in response to the first at least one wavelength of light and urge the first end away from the second end in response to the second at least one wavelength of light. The movement transducer and the second at least one transducer can be separated by a distance and coupled with at least one electrical conductor extending there between.

In many embodiments, the at least one transducer comprises at least one photodetector configured to receive the electromagnetic energy transmitted through the eardrum. The at least one photodetector may comprise a first photodetector and a second photodetector. The first end may comprise a first cross-sectional size and the at least one photodetector may comprise a second cross sectional size, and the second cross sectional size can be at least about twice the first cross sectional size. The device can extend from the first end to the second end in a first direction, and the at least one photodetector can extend in a second direction, such that the second direction is transverse to the first direction. For example, the detector can have a surface that extends in the second direction and along a plane perpendicular to the first direction.

In many embodiments, an optical coupler is disposed on the photodetector to receive light scattered by the eardrum and transmit the scattered light to the photodetector. The optical coupler may comprise an optically transmissive material and an optical surface to receive the scattered light, and the optical surface may comprise one or more of a frustum of a cone, a frustum of a pyramid, a concave surface, a toric surface, a cylindrical surface, a lenslet array, a spherical lenslet array, or a cylindrical lenslet array.

In many embodiments, the photodetector comprises a surface profile to fit the eardrum and wherein the surface profile comprises one or more of a frustum of a cone, a frustum of a pyramid, a concave surface, a concave spherical surface, or a concave cylindrical surface.

In many embodiments the device further comprises a first component comprising the first end and a second component comprising the second end. The first end is separated from the second end by a distance, and the at least one transducer is coupled to the first component and the second component to vary the distance so as to vibrate the ear. The first component may comprise a first mass and the second component may comprise a second mass, in which the first mass is greater than the second mass such that the second end moves more than the first end to decrease feedback when the at least one transducer vibrates the ear to transmit the sound to the user.

In many embodiments, a substantially rigid elongate structure extends between the first end and the second end to couple the first end to the second end, and the substantially rigid elongate structure may extend along an axis, for example. A mass can be coupled to the at least one transducer to move the mass opposite the substantially rigid elongate structure in response to the electromagnetic energy. The mass can be substantially contained within the substantially rigid elongate structure.

In many embodiments, device comprises a joint disposed between the first and the second end. The joint may comprise many joints and may comprise at least one of a ball and socket joint or a U-joint. The joint can be configured to rotate between the first end and the second end, which can improve safety. The joint can be configured to limit rotation of the first end relative to the second end. For example, the joint can be configured to limit rotation of the first end relative to the second end with a stop. The stop may comprise a first beveled surface of a first component of the joint configured to contact a second beveled surface of a second component of the joint so as to limit motion to within a predetermined range. The range may comprise, +/−30 degrees, for example. A second joint can be disposed between the first end and the second end. The second joint may comprise a telescopic joint, for example.

In another aspect, embodiments provide an active ossicular replacement device to transmit a sound to a user. At least one photodetector is configured to receive a light signal. A first component is configured to connect with at least one of an eardrum or a malleus of the ear, and the first component comprises a first end configure to orient toward the eardrum. A second component is configured to connect with a stapes of the ear, and the second component comprises a second end configured to orient toward the stapes opposite the first end. The first end is separated from the second end by a distance. A transducer is coupled to the at least one photodetector, the first component, and the second component, and the transducer is configured to change the distance from the first end to the second end in response to the light signal to vibrate the ear and transmit the sound to the user.

In many embodiments, the at least one detector comprises a first detector responsive to a first at least one wavelength of light and a second detector responsive to a second at least one wavelength of light, and the transducer is configured to urge the first end toward the second end to decrease the distance in response to the first at least one wavelength of the light and to urge the first end away from the second end to increase the distance in response to the second at least one wavelength of light.

In another aspect, embodiments provide a method of transmitting sound to an ear of a user. Electromagnetic energy is transmitted through the eardrum of the user to an active ossicular replacement device. The active ossicular replacement device is coupled to at least a stapes of the ear and vibrates in response to the electromagnetic energy transmitted through the eardrum.

In many embodiments, the active ossicular replacement device extends between at least one of a malleus or an eardrum of the ear and the stapes. The device may comprise a length extending between the at least one of the malleus or the eardrum and the stapes, and the length may increase in response to a first at least one wavelength of light and decrease in response to a second at least one wavelength of light so as to transmit the sound to the user.

In many embodiments, the device is coupled to the malleus between a head of the malleus and an umbo where the eardrum connects to the malleus, such that occlusion is decreased.

In another aspect, embodiments provide a method of providing an active ossicular placement device to an ear of a user, in which the ear has an eardrum. The active ossicular replacement device is placed in the middle ear with a first end connected to at least one of a malleus or an eardrum of the user and a second end connected to a stapes of the user. The active ossicular replacement device is configured to vibrate in response to electromagnetic energy transmitted through eardrum.

In many embodiments, the first end of the device is coupled to the malleus between a head of the malleus and an umbo where the eardrum connects to the malleus, such that occlusion is decreased.

In many embodiments, an incision is made in the eardrum and an incus is removed from the middle ear through the incision, and the active ossicular placement device is positioned on the stapes through the incision. The eardrum may comprise an annulus and the incision may extend at least partially within the annulus.

In many embodiments, the incision heals and the electromagnetic energy is transmitted through the eardrum when the incision has healed.

In another aspect embodiments provide a device to transmit sound to an ear of a user, in which the device comprises means for transmitting the sound to the ear of the user, and the means may comprise one or more of the components having corresponding function as described herein.

BRIEF DESCRIPTION OF THE DRAWINGS

FIG. 1E1 shows an active ossicular replacement assembly comprising an articulated joint;

FIG. 1E2 shows the transducer comprising the at least one photodetector, in which the first photodetector and the second photodetector have surfaces shaped to fit the eardrum TM;

FIG. 1E3 shows an optical coupler positioned on the at least one photodetector to couple the at least one detector to the light source and to receive light scattered transmitted through the tympanic membrane, in accordance with embodiments;

FIG. 1E4 shows the optical coupler comprising a plurality of lenslets disposed on the at least one detector, in accordance with embodiments;

FIG. 3 shows an experimental set up to determine light transmission through a human eardrum, in accordance with embodiments.

DETAILED DESCRIPTION OF THE INVENTION

As used herein, light encompasses electromagnetic radiation having wavelengths within the visible, infrared and ultraviolet regions of the electromagnetic spectrum.

In many embodiments, the hearing device comprises a photonic hearing device, in which sound is transmitted with photons having energy, such that the signal transmitted to the ear can be encoded with the transmitted light.

Figure 1A:
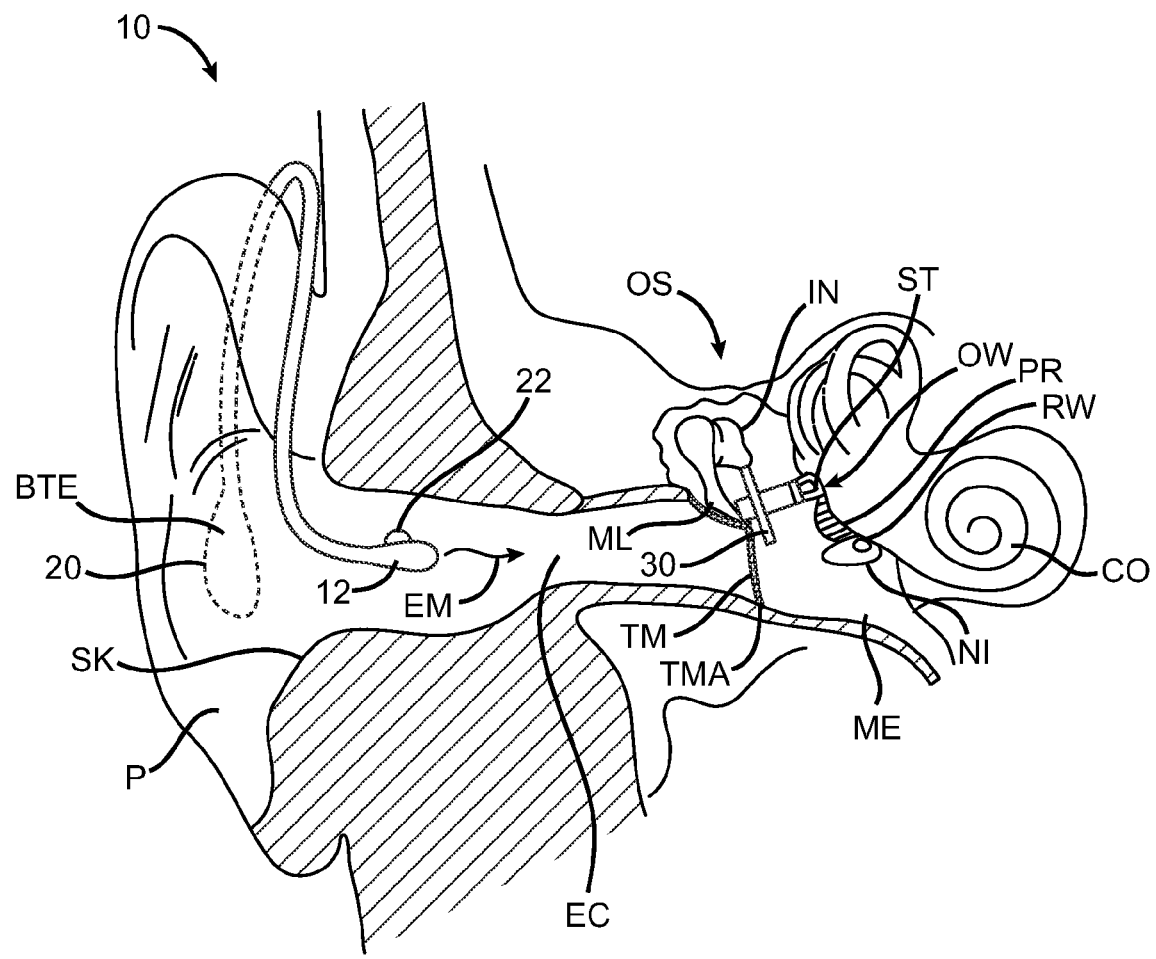
FIG. 1A shows a hearing aid system configured to transmit electromagnetic energy to an output transducer assembly comprising an active ossicular replacement prosthesis positioned in the middle ear, in accordance with embodiments of the present invention.

FIG. 1A shows a hearing aid system 10 configured to transmit electromagnetic energy to an output assembly 30 comprising an active ossicular replacement prosthesis (hereinafter "AORP") positioned in the middle ear ME of the user. The AORP can be useful with people having a mixed hearing loss in which a conductive hearing loss of the eardrum and ossicles occurs in combination with a sensorineural hearing loss of the cochlea. The AORP can be positioned in the ear so as to couple the eardrum to the cochlea. The AORP may comprise a passive mode, for example when no signal is transmitted and the AORP passively transmits vibration from the eardrum TM and malleus ML to the stapes ST. The AORP may also comprise an active mode, in which the AORP actively vibrates the cochlea CO with energy transmitted into the middle ear, such that a sound can be amplified to improve hearing of the user. The AORP may comprise known biocompatible materials, and can be hermetically sealed in a housing such that the electronics are encased and protected.

The ear comprises an external ear, a middle ear ME and an inner ear. The external ear comprises a Pinna P and an ear canal EC and is bounded medially by an eardrum TM. Ear canal EC extends medially from pinna P to eardrum TM. Ear canal EC is at least partially defined by a skin SK disposed along the surface of the ear canal. The eardrum TM comprises an annulus TMA that extends circumferentially around a majority of the eardrum to hold the eardrum in place. The middle ear ME is disposed between eardrum TM of the ear and a cochlea CO of the ear. The middle ear ME comprises the ossicles OS to couple the eardrum TM to cochlea CO. The ossicles OS comprise an incus IN, a malleus ML and a stapes ST. The malleus ML is connected to the eardrum TM and the stapes ST is connected to an oval window OW, with the incus IN disposed between the malleus ML and stapes ST. The AORP can replace the function of the incus IN and couple the malleus ML to the stapes ST. Stapes ST is coupled to the oval window OW so as to conduct sound from the middle ear to the cochlea.

The hearing system 10 includes an input transducer assembly 20 and an output transducer assembly 30 to transmit sound to the user. Hearing system 10 may comprise a behind the ear unit BTE. Behind the ear unit BTE may comprise many components of system 10 such as a speech processor, battery, wireless transmission circuitry and input transducer assembly 10. Behind the ear unit BTE may comprise many component as described in U.S. Pat. Pub. Nos. 2007/0100197, entitled "Output transducers for hearing systems"; and 2006/0251278, entitled "Hearing system having improved high frequency response", the full disclosures of which are incorporated herein by reference and may be suitable for combination in accordance with some embodiments of the present invention. The input transducer assembly 20 can be located at least partially behind the pinna P, although the input transducer assembly may be located at many sites. For example, the input transducer assembly may be located substantially within the ear canal, as described in U.S. Pub. No. 2006/0251278, the full disclosure of which is incorporated by reference. The input transducer assembly may comprise a blue tooth connection to couple to a cell phone and my comprise, for example, components of the commercially available Sound ID 300, available from Sound ID of Palo Alto, Calif.

The input transducer assembly 20 can receive a sound input, for example an audio sound. With hearing aids for hearing impaired individuals, the input can be ambient sound. The input transducer assembly comprises at least one input transducer, for example a microphone 22. Microphone 22 can be positioned in many locations such as behind the ear, as appropriate. Microphone 22 is shown positioned to detect spatial localization cues from the ambient sound, such that the user can determine where a speaker is located based on the transmitted sound. The pinna P of the ear can diffract sound waves toward the ear canal opening such that sound localization cues can be detected with frequencies above at least about 4 kHz. The sound localization cues can be detected when the microphone is positioned within ear canal EC and also when the microphone is positioned outside the ear canal EC and within about 5 mm of the ear canal opening. The at least one input transducer may comprise a second microphone located away from the ear canal and the ear canal opening, for example positioned on the behind the ear unit BTE. The input transducer assembly can include a suitable amplifier or other electronic interface. In some embodiments, the input may comprise an electronic sound signal from a sound producing or receiving device, such as a telephone, a cellular telephone, a Bluetooth connection, a radio, a digital audio unit, and the like.

In many embodiments, at least a first microphone can be positioned in an ear canal or near an opening of the ear canal to measure high frequency sound above at least about one 4 kHz comprising spatial localization cues. A second microphone can be positioned away from the ear canal and the ear canal opening to measure at least low frequency sound below about 4 kHz. This configuration may decrease feedback to the user, as described in U.S. Pat. Pub. No. US 2009/0097681, the full disclosure of which is incorporated herein by reference and may be suitable for combination in accordance with embodiments of the present invention.

Input transducer assembly 20 includes a signal output source 12 which may comprise a light source such as an LED or a laser diode, an electromagnet, an RF source, or the like. The signal output source can produce an output based on the sound input. Implantable output transducer assembly 30 can receive the output from input transducer assembly 20 and can produce mechanical vibrations in response. Implantable output transducer assembly 30 comprises a sound transducer and may comprise at least one of a coil, a magnet, a magnetostrictive element, a photostrictive element, or a piezoelectric element, for example. For example, the implantable output transducer assembly 30 can be coupled an input transducer assembly 20 comprising an elongate flexible support having a coil supported thereon for insertion into the ear canal as described in U.S. Pat. Pub. No. 2009/0092271, entitled "Energy Delivery and Microphone Placement Methods for Improved Comfort in an Open Canal Hearing Aid", the full disclosure of which is incorporated herein by reference and may be suitable for combination in accordance with some embodiments of the present invention. Alternatively or in combination, the input transducer assembly 20 may comprise a light source housed in the BTE and coupled to a fiber optic that extends into the ear canal, for example as described in U.S. Pat. Pub. No. 2006/0189841 entitled, "Systems and Methods for Photo-Mechanical Hearing Transduction", the full disclosure of which is incorporated herein by reference and may be suitable for combination in accordance with some embodiments of the present invention. The light fiber may comprise a distal end positioned in the ear canal to direct light through the eardrum, and a lens, for example a collimation optic may be positioned on the distal end of the fiber to illuminate a portion of the eardrum corresponding to the detector of the AORP. The light source of the input transducer assembly 20 may also be positioned in the ear canal, and the output transducer assembly and the BTE circuitry components may be located within the ear canal so as to fit within the ear canal. When properly coupled to the subject's hearing transduction pathway, the mechanical vibrations caused by output transducer 30 can induce neural impulses in the subject which can be interpreted by the subject as the original sound input.

The output transducer assembly 30 can be configured to couple to the hearing transduction pathway of the middle ear in many ways, so as to induce neural impulses which can be interpreted as sound by the user. The coupling may occur with the AORP coupled to the malleus ML and stapes ST. Vibration of eardrum TM transmits sound to cochlea CO with vibration of the ossicles induced by assembly 30.

The implantable assembly 30 comprising the AORP can be coupled to the malleus at a location of the manubrium between the umbo and the head of the malleus so as to decrease occlusion. The malleus may comprise motion that substantially pivots about head H. The leverage of the eardrum TM and the malleus ML on the AORP can be increased by coupling the AORP to the malleus at a location away from the umbo, for example a location away from the umbo between the umbo and head, for example near a lateral process of the malleus.

Figure 1B:
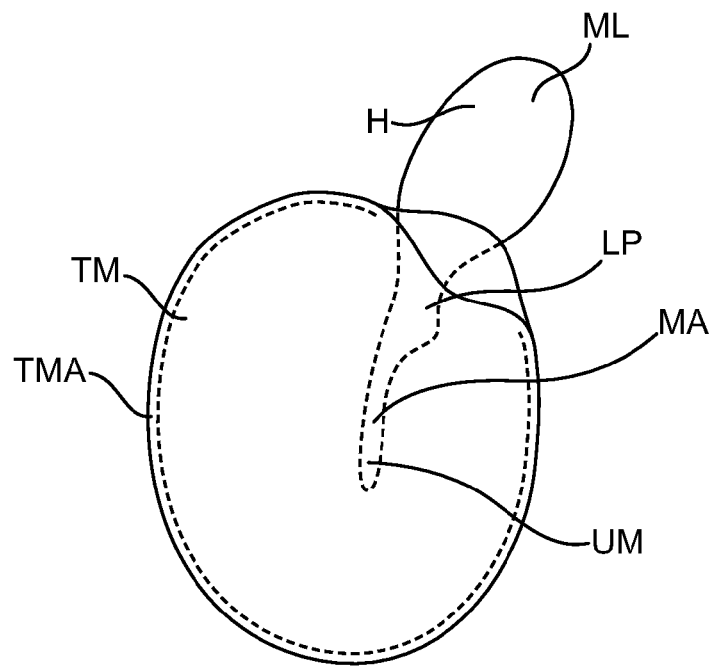
FIG. 1B shows the lateral side of the eardrum and FIG. 1C shows the medial side of the eardrum, suitable for incorporation of the hearing aid system of FIG. 1.
Figure 1C:
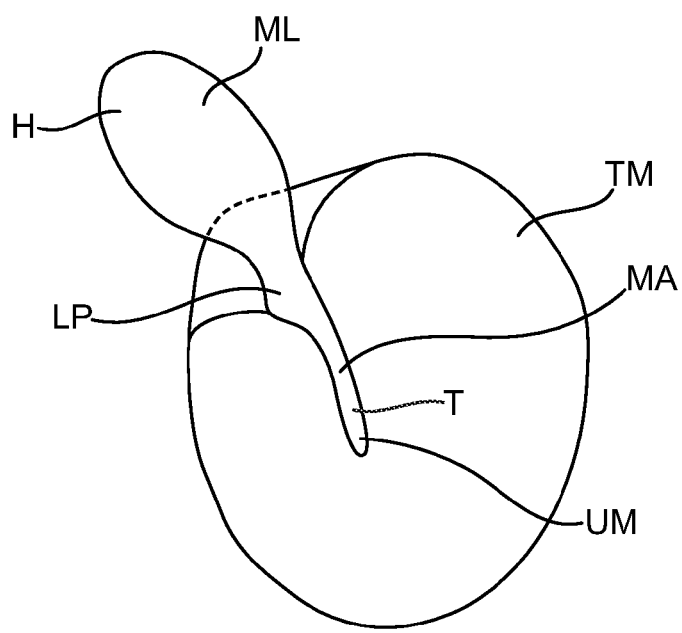

FIG. 1B shows structures of the ear on the lateral side of the eardrum TM. FIG. 1C shows structures of the ear on the medial side of the eardrum TM. The eardrum TM is connected to a malleus ML. Malleus ML comprises a head H, a manubrium MA, a lateral process LP, and a tip T. Manubrium MA is disposed between head H and tip T and coupled to eardrum TM, such that the malleus ML vibrates with vibration of eardrum TM.

Figure 1D:
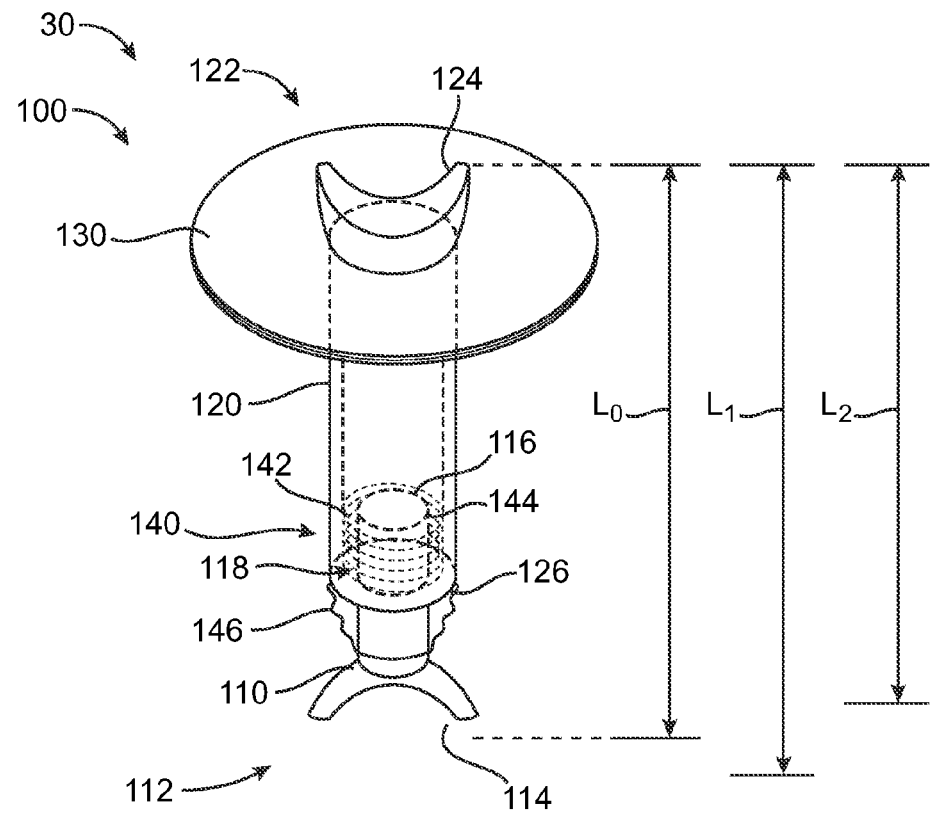
FIGS. 1D and 1E show a schematic illustration and side cross sectional view, respectively, of the active ossicular replacement prosthesis assembly of FIG. 1A.
Figure 1E:
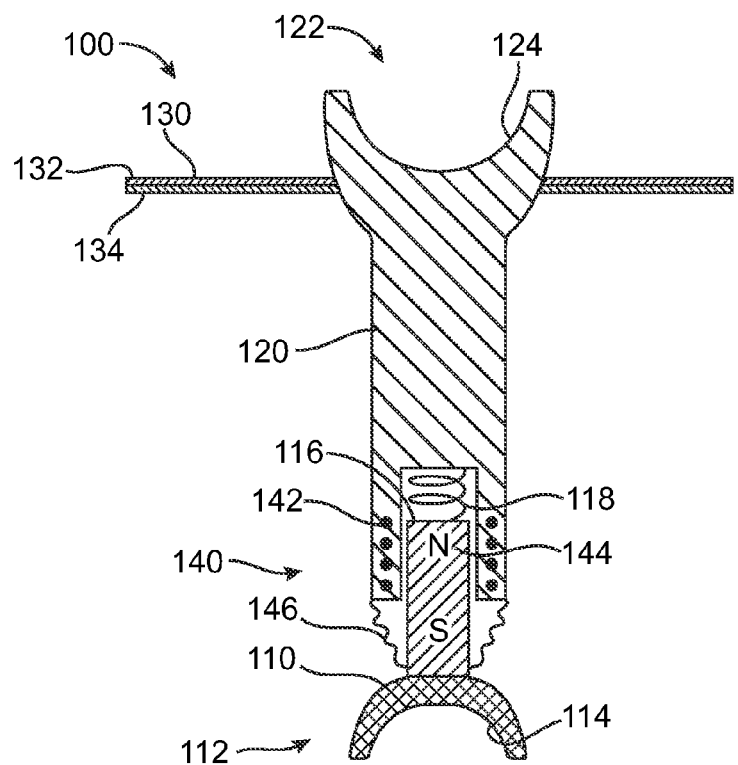

FIGS. 1D and 1E show a schematic illustration and side cross sectional view, respectively, of the AORP assembly 30 of FIG. 1A. The assembly 30 may comprise a variable length assembly 100 extending along an axis and sized to the user. Assembly 100 may comprise a medial component 110 configured to couple to the stapes and a lateral component 120 configured to coupled to at least one of the eardrum TM or the malleus. The medial component may have a first end portion 112 comprising a recess 114 formed thereon, and a second end 116 portion disposed opposite the first end portion. The lateral component 120 may comprise a first end portion 122 having a recess 124 formed thereon and a second end portion 126 disposed opposite the first end portion. A movement transducer 140 can be disposed between the medial component 110 and the lateral component 120. Movement transducer 140 can be coupled to a transducer 130 configured to receive electromagnetic energy. An electrical conductor, for example a wire, can extend between transducer 130 and movement transducer 140. Transducer 130 may comprise a coil, for example, to receive the signal transmitted wirelessly through the eardrum. Alternatively or in combination, transducer 130 may comprise at least one photodetector configured to drive movement transducer 140 in response to light signals transmitted wirelessly through the eardrum. Transducer 140 is configured to vary a length Lo extending between end 114 and end 124, such that the stapes vibrates in response to the electromagnetic energy. Transducer 140 may comprise a telescopic joint, in which a portion of the medial component slides inside a channel formed in the lateral component. For example, the length extending along the axis between end 114 and end 124 can increase from Lo to L1 and decrease to length L2, such that the stapes vibrates. The lateral component 120 may comprise a greater mass than medial component 110, such that medial component 110 vibrates move than lateral component 120. This can decrease feedback to microphone 22, as the cochlea CO can be vibrated a relatively greater amount than eardrum TM. The transducer 130 can be affixed to the lateral component 120 and the lateral component may comprise the transducer 130 such that the lateral component comprises at least about twice the mass of the medial component, for example at least about four times the mass of the medial component. A spring structure 118 may be coupled to the lateral component and the medial component to couple the lateral component to the medial component, and the spring 118 can be tuned with the lateral component and the medial component to a frequency response. The spring structure may be compressed when the AORP is installed, and can also provide safety, for example when the eardrum presses medially. The spring structure 118 may comprise many kinds of springs and may comprise an elastic material, for example an elastomer.

The assembly 100 can be sized to the user in many ways. For example, the surgeon can measure the ear of the user, and select the assembly 100 from among a plurality of assemblies based on the measurement of the user's ear and the length Lo. The length Lo of the assembly may comprise a length when no electromagnetic energy is transmitted to induce vibration.

Variable length AORP assembly 100 can be configured with at least one transducer in many ways so as to vibrate the cochlea CO such that the user perceives sound. For example, the at least one transducer may comprise movement transducer 140 comprising at least one of a piezoelectric transducer, a coil, a magnet, a balanced armature transducer, photostrictive material or a magnetostrictive material. The movement transducer can be positioned to couple to the lateral component and the medial component, for example between the two, such that the movement transducer can vary the length between the ends. For example, a photostrictive material can be disposed between the lateral component and the medial component and can extend outward similar to transducer 130 so as to receive light energy transmitted through eardrum TM. The movement transducer 140 may comprise a coil 142 affixed to the lateral component, and a magnet 144 positioned within coil 142. Alternatively, the lateral component may comprise the magnet and the medial component may comprise the coil. The assembly 100 may comprise a housing, and the housing may comprise a bellows 146 to allow the medial component 110 to slide relative to lateral component 120. The movement transducer 140 may comprise a coupling structure, for example a spring 148 or an elastomer, so as to couple the medial component 110 to lateral component 120 in the passive mode. The bellows may also be configured to coupled the medial component with the lateral component. The coupling structure may also comprise a tuning structure so as to provide a desired transfer function of the coupling of the medial component to the lateral component. The coupling structure can be used to tune the passive coupling and the active coupling of the lateral component to the medial component.

The transducer 130 may comprise at least one photodetector as noted above. For example, the at least one photodetector may comprise a first photodetector 132 and a second photodetector 134. The first photodetector 132 can be sensitive to a first at least one wavelength of light, and the second photodetector 134 can be sensitive to a second at least one wavelength of light. The first photodetector may transmit substantially the second at least one wavelength of light such that the first photodetector can be positioned over the second photodetector. The first photodetector 132 and the second photodetector 134 may be coupled to the movement transducer 140 with an opposite polarity such that the transducer urges the first component toward the second component so as to decrease the length in response to the first at least one wavelength of light and such that the transducer urges the first component away from the second component so as to increase the length in response to the second at least one wavelength of light.

The first light output signal and the second light output signal can drive the movement transducer in a first direction and a second direction, respectively, such that the cross sectional size of both detectors positioned on the assembly corresponds to a size of one of the detectors. The first detector may be sensitive to light comprising at least one wavelength of about 1 um, and the second detector can be sensitive to light comprising at least one wavelength of about 1.5 um. The first detector may comprise a silicon (hereinafter "Si") detector configured to absorb substantially light having wavelengths from about 700 to about 1100 nm, and configured to transmit substantially light having wavelengths from about 1400 to about 1700 nm, for example from about 1500 to about 1600 nm. For example, the first detector can be configured to absorb substantially light at 904 nm. The second detector may comprise an Indium Gallium Arsenide detector (hereinafter "InGaAs") configured to absorb light transmitted through the first detector and having wavelengths from about 1400 to about 1700 nm, for example from about 1500 to 1600 nm, for example 1550 nm. In a specific example, the second detector can be configured to absorb light at about 1310 nm. The cross sectional area of the detectors can be about 4 mm squared, for example a 2 mm by 2 mm square for each detector, such that the total detection area of 8 mm squared exceeds the cross sectional area of 4 mm squared of the detectors in the ear canal. The detectors may comprise circular detection areas, for example a 2 mm diameter circular detector area.

The first photodetector 132 and the second photodetector 134 may comprise at least one photovoltaic material such as crystalline silicon, amorphous silicon, micromorphous silicon, black silicon, cadmium telluride, copper indium gallium selenide, and the like. In some embodiments, at least one of photodetector 132 or photodetector 132 may comprise black silicon, for example as described in U.S. Pat. Nos. 7,354,792 and 7,390,689 and available under from SiOnyx, Inc. of Beverly, Mass. The black silicon may comprise shallow junction photonics manufactured with semiconductor process that exploits atomic level alterations that occur in materials irradiated by high intensity lasers, such as a femto-second laser that exposes the target semiconductor to high intensity pulses as short as one billionth of a millionth of a second. Crystalline materials subject to these intense localized energy events may under go a transformative change, such that the atomic structure becomes instantaneously disordered and new compounds are "locked in" as the substrate re-crystallizes. When applied to silicon, the result can be a highly doped, optically opaque, shallow junction interface that is many times more sensitive to light than conventional semiconductor materials. Photovoltaic transducers for hearing devices are also described in detail in U.S. Patent Applications Nos. 61/073,271, entitled "Optical Electro-Mechanical Hearing Devices With Combined Power and Signal Architectures"; and 61/073,281, entitled "Optical Electro-Mechanical Hearing Devices with Separate Power and Signal", the entire contents of which have been previously incorporated herein by reference and may be suitable for combination in accordance with some embodiments as described herein.

The electromagnetic signal transmitted through the eardrum TM to the assembly 100 may comprise one or more of many kinds of signals. For example, the signal transmitted through the eardrum TM may comprise a pulse width modulated signal. The pulse width modulated signal may comprise a first pulse width modulated signal of at least one first wavelength of light from a first source and the second pulse width modulated signal of a second at least one wavelength of light from a second source. The first at least one wavelength of light may be received by a first detector, and the second at least one wavelength of light may be received by the second detector.

The first end 112 can be shaped in many ways to couple to the stapes. The first end 112 can be configured to coupled to the head of the stapes or the footplate of the stapes. For example the first end 112 may comprise a recess 114 configured to couple to a head of the stapes. The first end 112 may comprise a flat surface to contact the footplate of the stapes, or a convex surface to contact the footplate of the stapes, or a combination thereof.

Recess 114 can be shaped in many ways to receive the head of the stapes. Recess 114 may comprise a concave shape and can be configured to couple to the head of the stapes ST. The recess can extend inwardly toward the movement transducer a maximum distance, and the inward maximum distance can be within a range from about 0.6 to 0.9 mm. The recess may comprise a maximum distance across, and the maximum distance across can be within a range from about 1.1 to about 1.3 mm.

Recess 124 can be shaped in many ways to receive the malleus and connect with at least one of the malleus or the eardrum TM. Recess 124 may comprise a concave shape and can be configured to couple to the at least one of the malleus ML or eardrum TM. The recess can extend inwardly toward the movement transducer a distance of no more than about 0.7 mm. The recess may comprise a maximum distance across within a range from about 0.7 mm to about 0.9 mm to couple to the malleus.

The components of the AORP may comprise many biocompatible materials, for example hydroxyapatite, titanium, polymer, or cobalt chrome, and many combinations thereof. The biocompatible material may comprise a material to promote bone growth. For example, the first end 112 may comprise hydroxyapatite and the second end 122 may comprise hydroxyapatite to couple to the respective ends to the stapes and malleus, respectively.

FIG. 1E1 shows an output transducer assembly 30 an AORP assembly 100 comprising an articulated joint, for example pivoting joint 160. The pivoting joint can facilitate insertion of the AORP. Alternatively to the pivoting joint, the articulated joint may comprise U-joints. The pivoting joint 160 may comprise a ball and socket joint. The ball and socket joint may comprise a ball 162 and a socket 166.

The articulated joint may have limited angle of rotation, for example +/−30 degrees. An inclined bevel 168 may extend from ball 168. An inclined bevel 166 may extend from socket 164. At the predetermined limit of rotation, the inclined bevel 168 may contact the inclined bevel 166 so as to limit the rotation.

The articulated joint may comprise spring structures or elastic structures, or both, so as to allow elastic pivoting with a slight load and so as to couple the eardrum to the stapes.

The articulated joint may be used in combination with transducer 140, as shown above. Alternatively, the articulated joint, for example pivoting joint 160 can be used with an AORP having a substantially fixed length, in which the pivoting joint is disposed between a first component having a substantially fixed length and a second component having a substantially fixed length, in which the second component comprises a transducer to vibrate at least the second component and the stapes.

FIG. 1E2 shows the transducer 130 comprising the at least one photodetector, in which the first photodetector 132 and the second photodetector 134 have surfaces shaped with a profile to fit the eardrum TM such that the photodetector can be positioned a distance from the eardrum within a range from about 0.5 to about 2 mm so as to couple efficiently to the light transmitted through the eardrum TM without contacting the eardrum, for example when the eardrum moves. The at least one surface of the photo detector may comprise one or more of many shapes so as to fit the eardrum. For example, the at least one surface of the photodetector may comprise a frustum of a truncated cone or a frustum of a pyramid, for example. Alternatively or in combination, the at least one detector may have a concave surface sized to fit the eardrum and the concave surface may comprise one or more of an aspheric concave surface, a spherical concave surface, a cylindrical concave surface, a toric concave surface, or combinations thereof.

Figure 3:
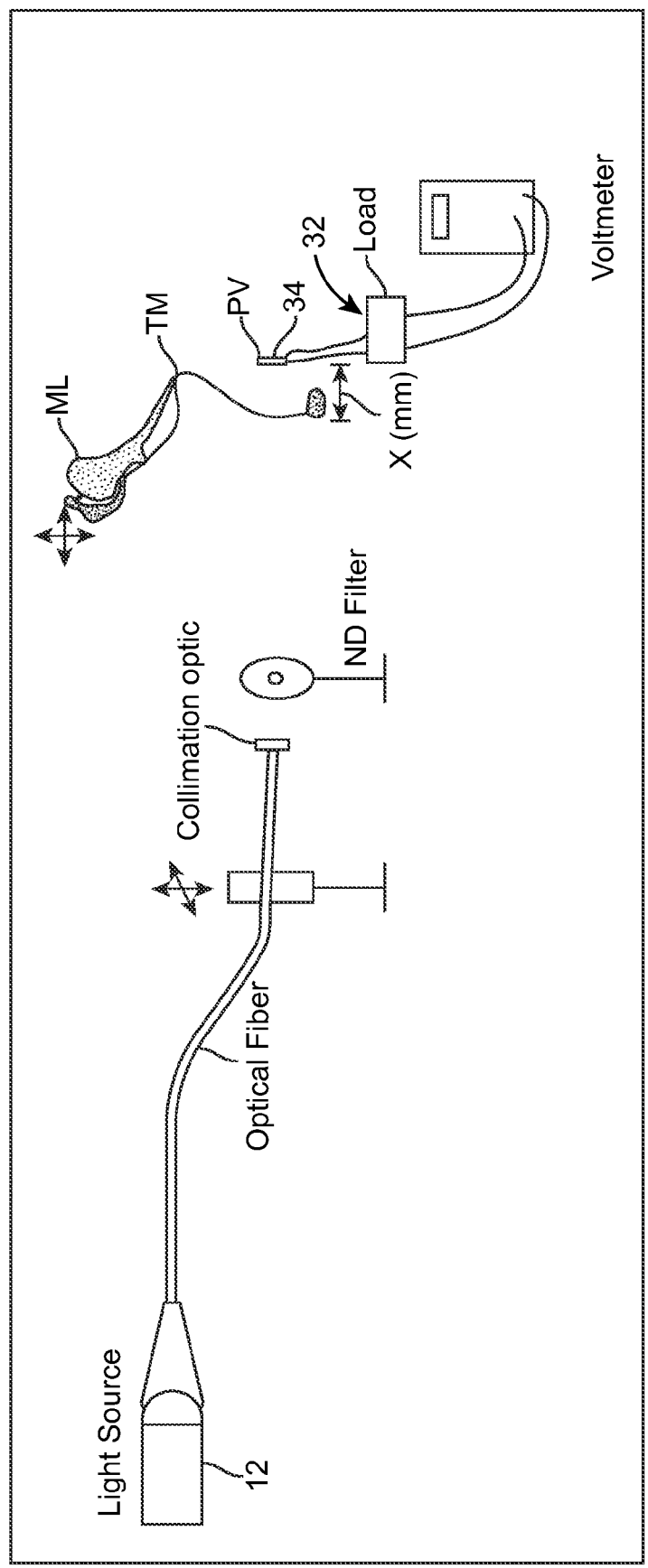

FIG. 1E3 shows an optical coupler 133 positioned on the at least one photodetector comprising the first photodetector 132 and the second photodetector 134 to couple the at least one detector to the light source and to receive light scattered transmitted through the tympanic membrane. The surface can be shaped with a profile to fit the eardrum TM such that the photodetector can be positioned a distance from the eardrum within a range from about 0.5 to about 2 mm so as to couple efficiently to the light transmitted through the eardrum TM without contacting the eardrum, for example when the eardrum moves. The coupler may comprise a surface profile corresponding to one or more of many shapes and may comprise an optically transmissive material have an optical surface disposed thereon to receive the light transmitted through the eardrum TM. For example, the optical surface of the coupler may comprise one or more of an inverted frustum of a cone, a frustum of a pyramid, a concave surface to fit the eardrum TM, an aspheric concave surface, a spherical concave surface, a cylindrical concave surface, a toric concave surface, a plurality of lenslets, or combinations thereof.

FIG. 1E4 shows the optical coupler 133 comprising a plurality of lenslets disposed on the at least one detector. The plurality lenslets may comprise one or more convex spherical lenslets, an array of convex spherical lenslets, convex cylindrical lenslets, an array of convex spherical lenslets, or combinations thereof, for example.

Figure 1F:
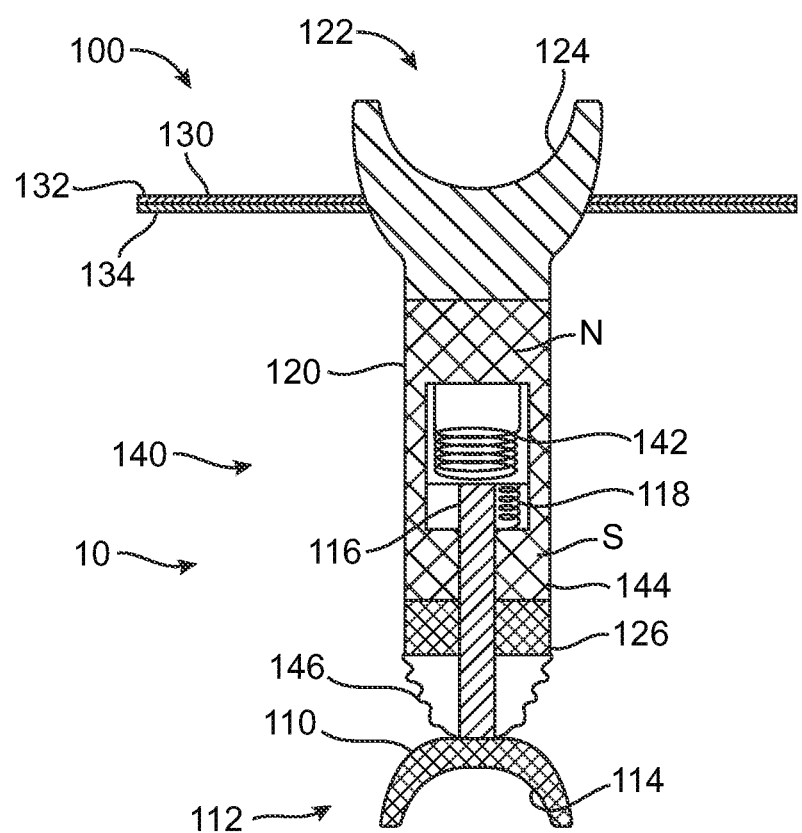
FIG. 1F shows the variable length AORP assembly configured with at least one transducer comprising the coil disposed at least partially between a north pole and a south pole of magnet, in accordance with embodiments.

FIG. 1F shows the variable length AORP assembly 100 configured with at least one transducer comprising the coil 142 disposed at least partially between a north pole and a south pole of magnet 144. The movement transducer can be positioned to couple to the lateral component and the medial component, for example between the two, such that the movement transducer can vary the length between the ends. The lateral component 120 comprises the magnet 144 and the medial component 110 comprises the coil 142. The assembly 100 may comprise the housing having bellows 146 to allow the medial component 110 to slide relative to lateral component 120.

Figure 1G:
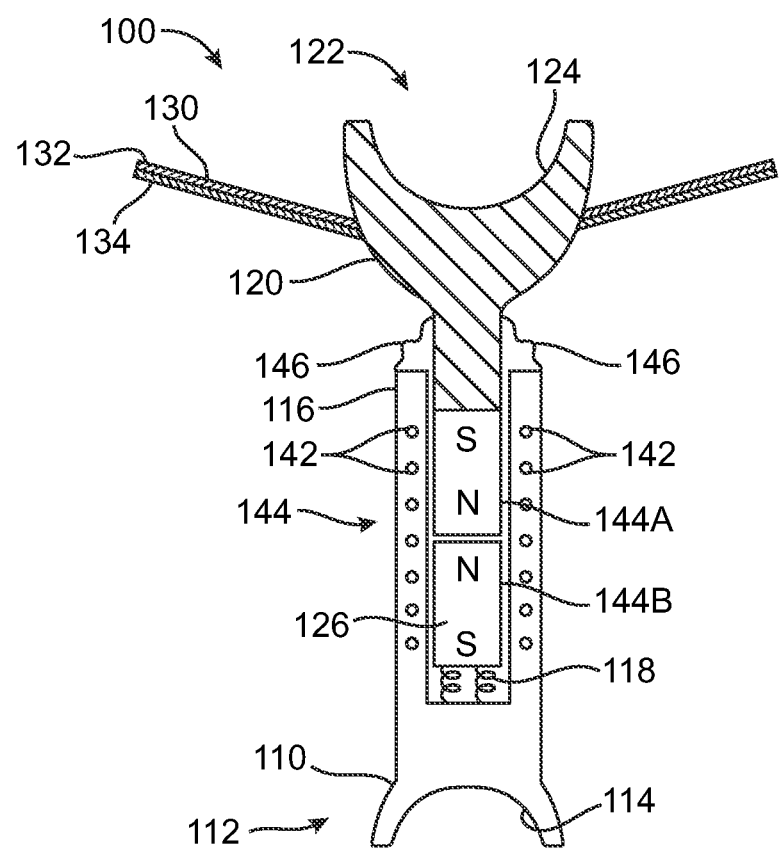
FIG. 1G shows the variable length AORP assembly configured with at least one transducer comprising the coil disposed in an outer annular casing comprising the coil extending around an inner cylindrical portion comprising pair of opposing magnets, in accordance with embodiments.

FIG. 1G shows the variable length AORP assembly 100 configured with transducer 140 comprising the coil 142 disposed in an outer annular casing comprising the coil extending around an inner cylindrical portion. The inner cylindrical portion comprises magnet 144, and magnet 144 may comprise pair of opposing magnets. The pair of opposing magnets may comprise a first magnet 144A and a second magnet 144B. The first and second magnets can be disposed along the axis such that the magnetic field of the first magnet opposes the magnetic field of the second magnet. The pair of opposing magnetic may increase the efficiency of the transducer and may provide decreased sensitivity to external magnetic fields, for example external magnetic fields that can be a source of noise and external magnetic fields such as with MRI machines. The coil can be electrically coupled to the first photodetector 132 and the second photodetector 134, so as to drive a current through the coil with the light energy from the photodetectors and drive the pair of magnets in response to the light signal. The embodiments as described herein above and below can be similarly configured with the pair of magnets and at least photodetector to pass current through the coil.

Figure 2A:
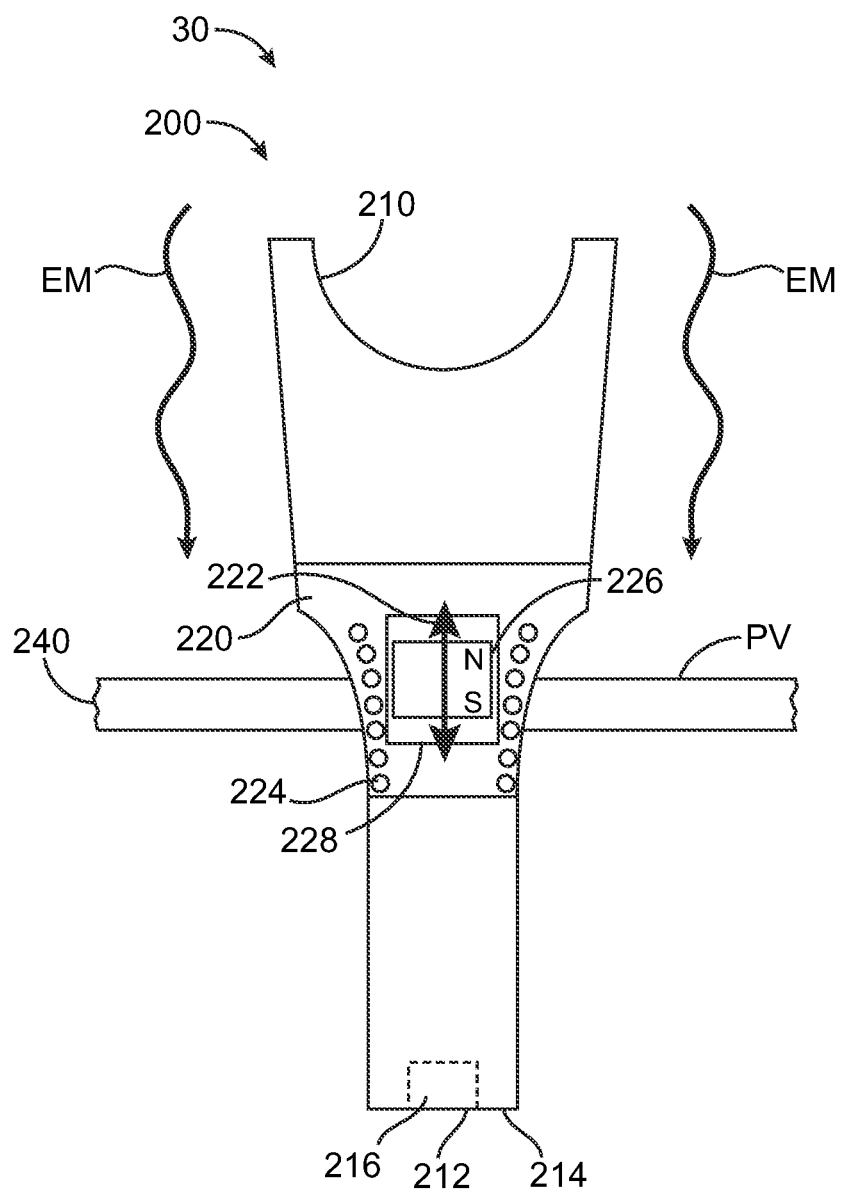
FIG. 2A shows a schematic illustration of an active ossicular replacement device, in accordance with embodiments of the present invention.

FIG. 2A shows a schematic illustration of a fixed length active ossicular replacement assembly 200. The assembly 30 may comprise a fixed length assembly 200, comprising a substantially rigid material extending from the first end to the second end. The fixed length AORP assembly 200 can be configured with at least one transducer in many ways so as to vibrated the cochlea CO such that the user perceives sound. Device 200 comprises a first end 210 configured to couple with at least one of the malleus ML or the eardrum TM. Assembly 200 comprises a second end 212 configured to couple to the stapes ST, for example to a footplate of the stapes. Assembly 200 comprises at least one transducer 240 configured to receive electromagnetic energy, as described above. Assembly 200 comprises at transducer 220 configured to vibrate at least the stapes of the ear in response to the electromagnetic energy.

The first end 210 can be configured in many ways to couple to at least one of the malleus and the eardrum TM. The first end 210 may comprise a concave surface shaped to receive at least a portion of the malleus. The concave surface can be shaped to receive at least a portion of a manubrium of the malleus extending between a head of the malleus and an umbo where the malleus connects to the eardrum.

A distance from the first end to the second end is within a range from about 2.5 mm to about 7 such that the assembly fits between the malleus and the stapes. The distance from the first end to the second end can be sized based on the characteristics of the user, for example based on in situ measurement during surgery, such that an appropriately sized device can be selected from among a plurality of incrementally sized devices available to the surgeon. In some embodiments, the at least one transducer 220 may extend and reduce the length so as to vibrate the stapes, as described below.

The second end 212 can be configured in many ways to couple to the stapes. For example, second end 212 may comprise an annular rim 214 that defines a channel 216 sized to receive the stapes. The annular rim 214 can contact a footplate FL of the stapes.

The at least one transducer 220 may comprise at least one of a piezoelectric transducer, a coil, a magnet, a balanced armature transducer, or a photostrictive material. The at least one transducer can be configured press against the stapes with mass from first portion of the device. For example, the at least one transducer 220 may comprise a transducer coupled to at least the medial end of the assembly 200 to drive the stapes in response to the electromagnetic energy. The at least one transducer 220 may comprise a coil 224 and a magnet 226 to induce vibration, as indicated with arrows 222. For example, the electromagnetic energy may comprise light incident on the at least one photodetector so as to drive a current through coil 224, so as to vibrate magnet 226. Magnet 226 may move along a channel 228 inside assembly 200. Magnet 226 may comprise sufficient mass such that force against the magnet from the coil can urges the coil relative to the magnet. The coil can be affixed to the assembly, such that the magnet moves relative to the assembly within channel 228. Alternatively, the magnet can be affixed to the assembly and the coil may move relative to the assembly.

The assembly 200 may comprise a rigid material extending from the lateral end to the medial end, and may comprise one or more of many biocompatible materials, for example hydroxyapatite, titanium, polymer, cobalt chrome, and many combinations thereof. The assembly 200 may comprise a substantially constant length. The lateral end 210 and medial end 214 of assembly 200 may vibrate together and in opposition to an internal mass of the at least one transducer 220, for example in opposition to an internal mass comprising magnet 226 as described above, such that the user perceives sound.

The at least one transducer may comprise a second at least one transducer 240 configured to receive electromagnetic energy convert the electromagnetic energy to electrical energy to drive the at least one first transducer. The second at least one transducer may comprise a coil or a photodetector, or both, configured to receive the electromagnetic energy EM transmitted through the eardrum TM. For example, the second at least one transducer 240 may comprise at least one photodetector configured to receive the electromagnetic energy transmitted through the eardrum. The at least one photodetector may comprise a first photodetector and a second photodetector. The first end may comprise a first cross-sectional size and the at least one photodetector may comprise a second cross sectional size, and the second cross sectional size can be at least about twice the first cross sectional size. The device can extend from the first end to the second end in a first direction, and the at least one photodetector can extend in a second direction, such that the second direction is transverse to the first direction. For example, the detector can extends substantially along a plane, such that the plane extends perpendicular to the first direction.

Figure 2B:
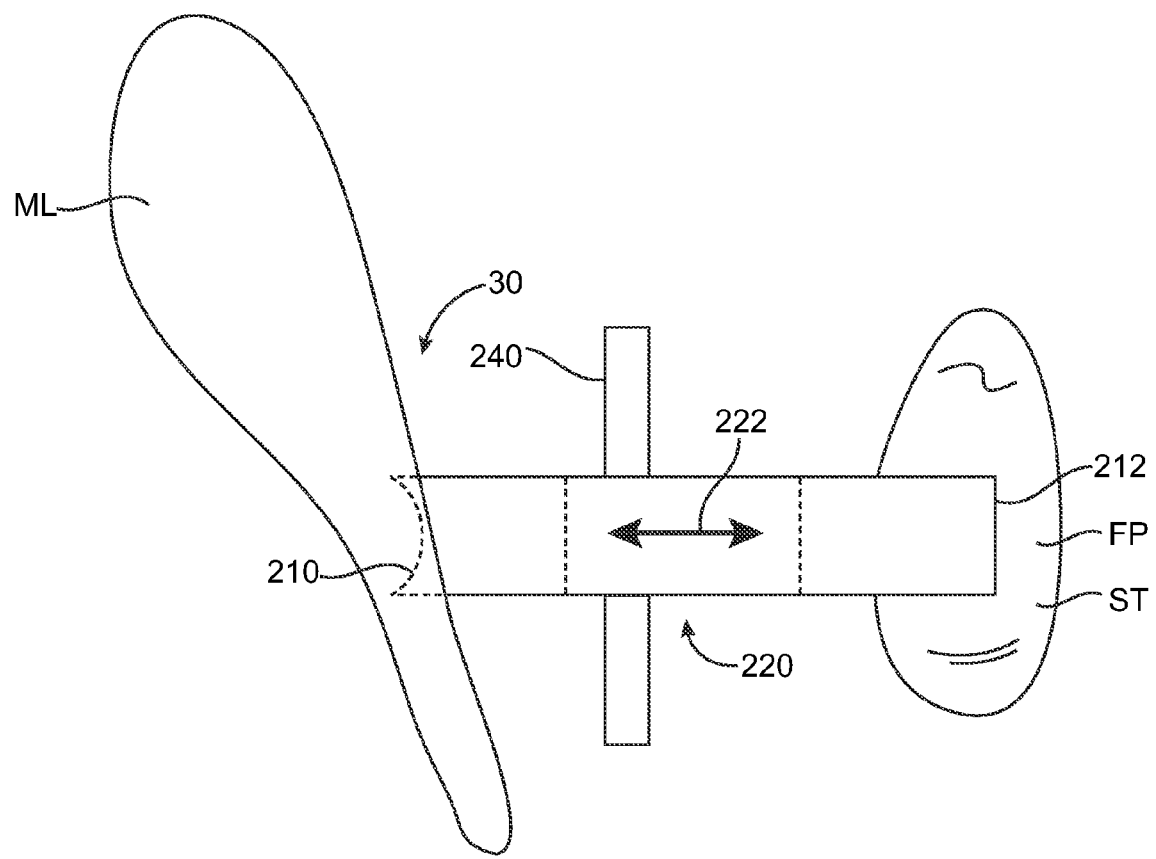
FIG. 2B shows the active ossicular replacement device as in FIG. 2A positioned between a malleus and a stapes.

FIG. 2B shows the active ossicular replacement device as in FIG. 2A positioned between a malleus and a stapes. First end 210 is shown in contact with malleus ML. Alternatively or in combination, first end 210 may contact at least a portion of tympanic membrane TM. Second end 212 may contact footplate FL of stapes ST to couple the second end to the stapes ST. The assembly 200 may comprise a length sized to the user, for example based on a measurement of the user's middle ear such as distance from annulus TMA of the eardrum TM to the footplate of the stapes ST.

Figure 2C:
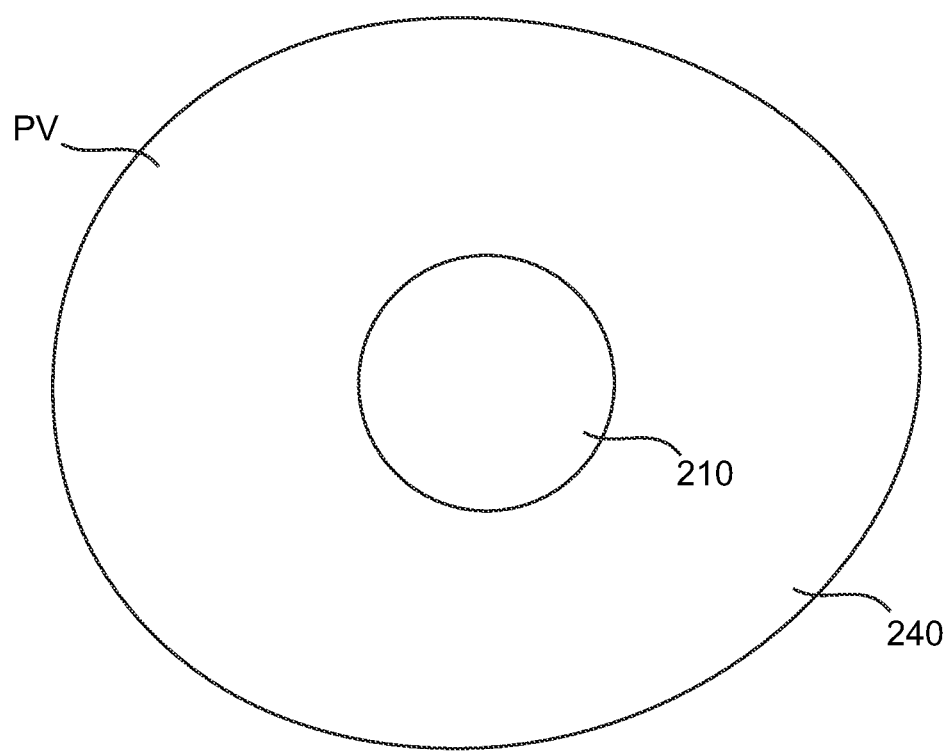
FIG. 2C shows an end view of the active ossicular replacement device as in FIG. 2A.

FIG. 2C shows an end view of the active ossicular replacement device as in FIG. 2A. At least one transducer 240 may comprise an annular configuration extending radially outward beyond first end 210 so as to receive the electromagnetic energy.

The above described prostheses and the components thereof can be made with one or more of many biocompatible materials, for example one or more of hydroxyapatite, HAPEX™, titanium, plastic, or fluoroplastic.

Human Eardrum Transmission Experiment

The below described experiment was conducted to measure transmission of infrared light through the eardrum and determine arrangements of the input assembly 20 and output assembly 30.

Objective: To determine the amount of light transmission loss through a human eardrum at posterior, inferior and anterior positions and the amount of scatter by the eardrum.

Procedure: A fiber optic coupled laser diode light source was aligned with a photodiode optical detector. An eardrum was placed in line and the change in optical output from the photodiode determined. FIG. 3 shows the experimental setup. The eardrum is mounted to a x, y, z translation stage which allows a change to different positions of the eardrum that the light goes through.

Materials:

Light source—1480 nm laser diode coupled to a fiber (250 um diameter, 80 um core);

PhotoDiode—1480 nm photodiode (5.5 mm2);

Load—RLC electrical circuit equivalent to that of a balanced armature transducer coupled to a diaphragm, for example as commercially available from Knowles;

Collimation optics and a Neutral Density Filter (NE20B);

DC Voltmeter (Fluke 8060A);

Translation stages; and

Human cadaver eardrum with attached malleus (incus and other medial components removed)

Results

No Tympanic Membrane

The current was set such that the photodiode was in the saturation region. A neutral density (ND) filter was used to attenuate the light output to reduced the PD response. The measurements indicate that the ND filter attenuated the light source by 20.5 dB. This ensured that all measurements reported are from the linear region.

The photodiode voltage in response to the collimated light beam without the eardrum was measured at the beginning of the measurements and at the end of experiment. The difference was less than 1%.

With no TM and ND filter, the output in mV was 349. With the ND filer and no TM, this output decreased to within a range from about 32.9 to 33.1, corresponding to a linear change of 0.095 and −20.5 dB.

With Tympanic Membrane

Measurements were made at anterior, inferior, and posterior positions of the eardrum. The eardrum was moved at different locations relative to the photodiode and it's distance X (in mm) approximated. Table 1 shows the measured voltages corresponding to the different positions and different eardrum locations.

TABLE 1

Measured photodiode voltages corresponding to transmission loss from the eardrum.

|  | x (mm) | | | | |
| --- | --- | --- | --- | --- | --- |
|  | 0.1 | 0.5 | 1 | 2 | 3 |
| Posterior | 28 mV | 26.6 mV | 25.4 mV | 23.4 mV | 20.6 mV |
| Inferior |  |  | 23.6 mV | 21.1 mV | 17.1 mV |
| Anterior |  |  | 21.4 mV | 20.2 mV | 18.2 mV |

The posterior placement shows the highest voltage for all distances and has values of 28, 26.6, 25.4 23.4 and 20.6 mV for distances of 0.1, 0.5, 1, 2 and 3 mm, respectively.

For each eardrum position and location, the optical fiber was adjusted to maximize the PD voltage. This ensured that the light beam was maximally on the photodiode surface and that the measured response was due to transmission loss and not due to misalignments.

Calculations

The measured voltages were converted to percent transmission loss (hereinafter "TL") as follows:

$$\% \, TL = ((V_{NoTM} - V_{WithTM})/V_{NoTM}) * 100$$

where $V_{NoTM}$ is the measured voltage with no tympanic membrane and $V_{WithTM}$ is the measured voltage with the tympanic membrane Table 2 below shows the calculated % Transmission Loss using the above equation.

TABLE 2

PerCent Transmission loss

|  | x (mm) | | | | |
| --- | --- | --- | --- | --- | --- |
|  | 0.1 | 0.5 | 1 | 2 | 3 |
| Posterior | 16 | 20 | 23 | 29 | 38 |
| Inferior |  |  | 29 | 36 | 48 |
| Anterior |  |  | 35 | 39 | 45 |
| Average |  |  | 29 | 35 | 44 |

At all locations the posterior placement showed the least transmission loss and values of 16, 20, 23, 29 and 38% at distances of 0.1, 0.5, 1, 2 and 3 mm, respectively.

With the PD very close to the eardrum (within about 0.1 mm), the TL is about 16%. The TL could only be measured for the Posterior position.

Of the three positions of the eardrum, the posterior position is better than the inferior position by 6-10%, and better than the anterior position by 7-12%.

As the eardrum is moved away from the PD, the transmission loss increases linearly for all three positions. The transmission loss is about 29%, 35%, and 44% averaged across the three different positions for each of the 1, 2 and 3 mm locations respectively.

Experimental Conclusions

The transmission loss due to the eardrum is lowest at the posterior position (16%). The loss increases as the photodiode is moved away from the eardrum due to scatter of the collimated beam by the eardrum. At 3 mm from the eardrum, the average loss was as much as 44%. These data shown the unexpected result that there is more loss due to light scatter at angles away from the detector surface induced by the eardrum than due to transmission of light through the eardrum, and the detector and coupler such as a lens can be shaped appropriately so as to collect transmitted light scattered by the eardrum. These data also show the unexpected result that light transmission is higher through the posterior portion of the eardrum.

As the eardrum can move, the detector in a living person should be at least about 0.5 mm from the eardrum. The data suggest that a detector and/or component such as a lens can be shaped to fit the eardrum and provide improved transmission, for example shape with one or more of an inclined surface, a curved surface, and can be positioned within a range from about 0.5 mm to about 2 mm, for example.

The above data shows that illuminating a portion of the eardrum and placing a detector near the illuminated portion, for example, can achieve transmission coupling efficiency between the projected light beam and detector of a least about 50% (corresponding to 50% loss), for example at least about 60% (corresponding to 40% loss). These unexpectedly high results for coupling efficiency indicate that illumination of a portion of the eardrum and a detector sized to the illuminated portion can provide efficiencies of at least about 50%. Also, the optical fiber can be positioned in the ear canal without collimation optics such that light is emitted directly into the ear canal from the end of the optical fiber, and the optical fiber may be positioned in proximity to the photodetector, for example.

While the above is a complete description of the preferred embodiments of the invention, various alternatives, modifications, and equivalents may be used. Therefore, the above description should not be taken as limiting in scope of the present invention, which is defined solely by the appended claims and the full scope of the equivalents thereof.

What is claimed is:

1. An ossicular replacement device, the device comprising:
   a lateral component comprising a first end configured to connect with a malleus of an ear, the lateral component comprising a first mass;
   a medial component comprising a second end configured to connect with a stapes of the ear, the medial component comprising a second mass, the first end opposite the second end, the first end separated from the second end by a distance; and
   at least one output transducer configured to vibrate at least the second end in response to an electromagnetic energy driving signal;
   wherein the at least one output transducer, the lateral component and the medial component are discrete components, coupled to each other, and configured to provide a passive mode and an active mode, in the passive mode the device passively transmits vibration from the malleus to the stapes when no driving signal is transmitted to the at least one output transducer and in the active mode the device actively vibrates the stapes with an amplified energy from an energy sensing device when the driving signal is transmitted to the at least one output transducer in order to transmit the sound to a user; and wherein the at least one output transducer is coupled to the lateral component and the medial component to vary the distance in order to vibrate the ear and wherein the first mass is greater than the second mass in order to move the second end more than the first end to decrease feedback when the at least one output transducer varies the distance and vibrates the stapes to transmit the sound to the user.

2. The device of claim 1 wherein the at least one transducer is configured to receive electromagnetic energy transmitted through tissue of the user.

3. The device of claim 2 wherein the tissue comprises tissue of an eardrum of the user.

4. The device of claim 1 wherein the first end comprises a recess shaped to receive at least a portion of the malleus.

5. The device of claim 4 wherein the recess comprises a concave surface shaped to receive at least a portion of a manubrium of the malleus extending between a head of the malleus and an umbo.

6. The device of claim 4 wherein the recess extends inward a maximum distance of no more than about 0.6 mm to receive the portion of the manubrium and wherein the recess comprises a width within a range from about 0.7 mm to about 0.9 mm.

7. The device of claim 1 wherein the second end is shaped to couple a head of the stapes.

8. The device of claim 7 wherein the second end comprises a recess shaped to couple the head of the stapes.

9. The device of claim 8 wherein the recess extends inward a distance within a first range from about 0.6 mm to about 0.9 mm and wherein the recess comprises a distance across within a second range from about 1.1 mm to about 1.3 mm.

10. The device of claim 7 wherein the second end is shaped to couple a footplate of the stapes.

11. The device of claim 10 wherein the second end comprises at least one of a flat surface or a convex surface to couple to the footplate of the stapes.

12. The device of claim 1 wherein the at least one transducer comprises a movement transducer comprising at least one of a piezoelectric transducer, a coil, a magnet, a balanced armature transducer, or a photostrictive material.

13. The device of claim 12 wherein the at least one transducer further comprises a second at least one transducer configured to receive electromagnetic energy transmitted through the eardrum, the second at least one transducer comprising at least one of a photodetector or a coil configured to receive the electromagnetic energy transmitted through the eardrum.

14. The device of claim 13 wherein the second at least one transducer comprises the photodetector and wherein the electromagnetic energy transmitted through the eardrum comprises light.

15. The device of claim 14 wherein the photodetector comprises a first photodetector configured to receive a first at least one wavelength of light and a second photodetector configured to receive a second at least one wavelength of light and wherein the first photodetector and the second photodetector are coupled to the movement transducer to urge the first end toward the second end in response to the first at least one wavelength of light and urge the first end away from the second end in response to the second at least one wavelength of light.

16. The device of claim 15 wherein the movement transducer and the second at least one transducer are configured to be separated by a distance and coupled with at least one electrical conductor extending there between.

17. The device of claim 14 wherein the first end comprises a first cross-sectional size and the photodetector comprises a second cross sectional size and wherein the second cross sectional size is at least about twice the first cross sectional size.

18. The device of claim 14 wherein the device extends from the first end to the second end in a first direction and wherein the photodetector extends in a second direction, the second direction transverse to the first direction.

19. The device of claim 18 wherein the photodetector has a surface that extends in the second direction and along a plane substantially perpendicular to the first direction.

20. The device of claim 1, wherein the first end is further configured to connect with an eardrum of the ear.

21. An ossicular replacement device to transmit a sound to a user, the device comprising:
at least one photodetector configured to receive a light signal;
a lateral component configured to connect with a malleus of an ear, the lateral component comprising a first end configured to orient toward an eardrum;
a medial component configured to connect with a stapes of the ear, the medial component comprising a second end configured to orient toward the stapes opposite the first end, the first end separated from the second end by a distance; and
a transducer coupled to the at least one photodetector, the lateral component, and the medial component wherein the at least one photodetector, the lateral component and the medial component are discrete components, coupled to each other, and configured to provide a passive mode and an active mode, in the passive mode the device passively transmits vibration from the malleus to the stapes when no electromagnetic energy driving signal is transmitted to the at least one photodetector and in the active mode the device actively vibrates the stapes with an amplified energy from the at least one photodetector when the driving signal is transmitted to the at least one photodetector in order to transmit sound to the user.

22. The device of claim 21 wherein the first end, the second end and the transducer comprise an assembly configured for placement in a middle ear between the malleus and the stapes.

23. The device of claim 22 wherein a distance from the first end to the second end is within a range from about 2.5 mm to about 7 mm such that the assembly fits between the malleus and the stapes.

24. The device of claim 21 wherein an optical coupler is disposed on the at least one photodetector to receive light scattered by an eardrum and transmit the scattered light to the at least one photodetector.

25. The device of claim 24, wherein the optical coupler comprises an optically transmissive material and an optical surface to receive the scattered light, the optical surface comprising one or more of a frustum of a cone, a frustum of a pyramid, a concave surface, a toric surface, a cylindrical surface, a lenslet array, a spherical lenslet array, or a cylindrical lenslet array.

26. The device of claim 21 wherein the at least one photodetector comprises a surface profile to fit the eardrum and wherein the surface profile comprises one or more of a frustum of a cone, a frustum of a pyramid, a concave surface, a concave spherical surface, or a concave cylindrical surface.

27. The device of claim 21 further comprising a substantially rigid elongate structure extending between the first end and the second end to couple the first end to the second end.

28. The device of claim 27 further comprising a mass coupled to the at least one transducer to move the mass opposite the substantially rigid elongate structure in response to light energy.

29. The device of claim 28 wherein the mass is substantially contained within the substantially rigid elongate structure.

30. The device of claim 21 further comprising a joint disposed between the first and the second end.

31. The device of claim 30 wherein the joint comprises at least one of a ball and socket joint or a U-joint.

32. The device of claim 30 wherein the joint is configured to rotate between the first end and the second end.

33. The device of claim 30 wherein the joint is configured to limit rotation of the first end relative to the second end.

34. The device of claim 33 wherein the joint is configured to limit rotation of the first end relative to the second end with a stop.

35. The device of claim 34 wherein the stop comprises a first beveled surface of a first component of the joint configured to contact a second beveled surface of a second component of the joint to limit motion to within a predetermined range.

36. The device of claim 35 wherein the range comprises +/−30 degrees.

37. The device of claim 30 further comprising a second joint disposed between the first end and the second end.

38. The device of claim 37 wherein the second joint comprises a telescopic joint.

39. The device of claim 21 wherein the at least one photodetector comprises a first detector responsive to a first at least one wavelength of light and a second detector responsive to a second at least one wavelength of light and wherein the transducer is configured to urge the first end toward the second end to decrease the distance in response to the first at least one wavelength of the light and to urge the first end away from the second end to increase the distance in response to the second at least one wavelength of light.

40. The device of claim 39 wherein the first detector is coupled to the transducer with a first polarity and the second detector is coupled to the transducer with a second polarity opposite the first polarity.

41. The device of claim 21, wherein the lateral component is further configured to connect with an eardrum of the ear.

42. The device of claim 21, wherein the transducer is configured to vary the distance from the first end to the second end in response to the light signal.

43. A device to transmit sound to an ear of a user, the device comprising:
- a lateral component comprising a first end configured to connect with a malleus of the ear;
- a medial component comprising a second end configured to connect with a stapes of the ear;
- wherein said lateral and medial components are discrete components;
- means for a passive mode to passively transmit vibration from the malleus to the stapes wherein in the passive mode the device passively transmits vibrations when no electromagnetic energy driving signal is transmitted to at least one output transducer; and
- means for an active mode to actively vibrate the stapes with an amplified energy from an energy sensing device when the driving signal is transmitted to the at least one output transducer and moving the second end more than the first end to decrease feedback when the at least one transducer vibrates the stapes to transmit the sound to the user.

44. The device of claim 43, wherein the at least one output transducer is further configured to connect with an eardrum of the ear.

* * * * *